(12) United States Patent
Chase et al.

(10) Patent No.: US 9,366,738 B2
(45) Date of Patent: Jun. 14, 2016

(54) SELECTIVE SAMPLING MAGNETIC RESONANCE-BASED METHOD FOR ASSESSING STRUCTURAL SPATIAL FREQUENCIES

(71) Applicant: bioProtonics LLC, Santa Ynez, CA (US)

(72) Inventors: David R. Chase, Santa Barbara, CA (US); Timothy W. James, Santa Barbara, CA (US); Kristin M. James, Santa Barbara, CA (US)

(73) Assignee: bioProtonics, L.L.C, Santa Ynez, CA (US)

( * ) Notice: Subject to any disclaimer, the term of this patent is extended or adjusted under 35 U.S.C. 154(b) by 0 days.

(21) Appl. No.: 14/840,327

(22) Filed: Aug. 31, 2015

(65) Prior Publication Data

US 2016/0061917 A1    Mar. 3, 2016

Related U.S. Application Data

(60) Provisional application No. 62/044,321, filed on Sep. 1, 2014, provisional application No. 62/064,206, filed on Oct. 15, 2014, provisional application No. 62/107,465, filed on Jan. 25, 2015.

(51) Int. Cl.
| | |
|---|---|
| *G01V 3/00* | (2006.01) |
| *G01R 33/48* | (2006.01) |
| *G01R 33/54* | (2006.01) |
| *G01R 33/385* | (2006.01) |
| *A61B 5/00* | (2006.01) |
| *A61B 5/055* | (2006.01) |

(52) U.S. Cl.
CPC ............ *G01R 33/4818* (2013.01); *A61B 5/055* (2013.01); *A61B 5/7207* (2013.01); *G01R 33/385* (2013.01); *G01R 33/54* (2013.01)

(58) Field of Classification Search
CPC ...................................................... G01R 33/381
USPC .................................................. 324/307, 309
See application file for complete search history.

(56) References Cited

U.S. PATENT DOCUMENTS

| | | | | |
|---|---|---|---|---|
| 5,565,777 | A * | 10/1996 | Kanayama et al. | ........... 324/309 |
| 7,903,251 | B1 | 3/2011 | Farr et al. | |
| 7,932,720 | B2 | 4/2011 | James et al. | |
| 9,097,777 | B2 * | 8/2015 | Weber et al. | |
| 2014/0205541 | A1 | 7/2014 | James et al. | |
| 2014/0303487 | A1 * | 10/2014 | James et al. | .................. 600/415 |

\* cited by examiner

*Primary Examiner* — Louis Arana
(74) *Attorney, Agent, or Firm* — Felix L. Fischer

(57) ABSTRACT

The disclosed embodiments provide a method for acquiring MR data at resolutions down to tens of microns for application in in-vivo diagnosis and monitoring of pathology for which changes in fine tissue textures can be used as markers of disease onset and progression. Bone diseases, tumors, neurologic diseases, and diseases involving fibrotic growth and/or destruction are all target pathologies. Further the technique can be used in any biologic or physical system for which very high-resolution characterization of fine scale morphology is needed. The method provides rapid acquisition of selected values in k-space, with multiple successive acquisitions of individual k-values taken on a time scale on the order of microseconds, within a defined tissue volume, and subsequent combination of the multiple measurements in such a way as to maximize SNR. The reduced acquisition volume, and acquisition of only select values in k-space along selected directions, enables much higher in-vivo resolution than is obtainable with current MRI techniques.

20 Claims, 10 Drawing Sheets

SELECTIVE SAMPLING MAGNETIC RESONANCE-BASED METHOD FOR ASSESSING STRUCTURAL SPATIAL FREQUENCIES

REFERENCE TO RELATED APPLICATIONS

This application relies on the priority of U.S. provisional application Ser. No. 62/044,321 filed on Sep. 1, 2014 entitled SELECTIVE SAMPLING MAGNETIC RESONANCE-BASED METHOD FOR ASSESSING STRUCTURAL SPATIAL FREQUENCIES, Ser. No. 62/064,206 filed on Oct. 15, 2014 having the same title and Ser. No. 62/107,465 filed on Jan. 25, 2015 entitled micro-Texture Characterization by MRI.

BACKGROUND

1. Field of the Invention

The herein claimed method relates to the field of diagnostic assessment of fine textures in biological systems for pathology assessment and disease diagnosis, and in material and structural evaluation in industry and in engineering research. More specifically, the invention employs a method for repeat measurement of k-values associated with the spatial organization of biologic tissue texture, with the MRI machine gradients turned off. This allows assessment of tissue texture on a time-scale on the order of a msec, whereby the problem of patient motion becomes negligible. The method enables in vivo assessment, towards diagnosis and monitoring, of disease and therapy-induced textural changes in tissue. Representative targets of the technique are: 1) for assessment of changes to trabecular architecture caused by bone disease, allowing assessment of bone health and fracture risk, 2) evaluation of fibrotic development in soft tissue diseases such as, for example, liver, lung, and heart disease, and 3) changes to fine structures in neurologic diseases, such as the various forms of dementia, or in cases of brain injury and downstream neuro-pathology as in, for example, Traumatic Brain Injury (TBI) and Chronic Traumatic Encephalopathy (CTE), or for characterization and monitoring of abnormal neurologic conditions such as autism and schizophrenia. Other pathology applications include assessment of vascular changes such as in in the vessel network surrounding tumors or associated with development of CVD (Cerebrovascular Disease), and of changes in mammary ducting in response to tumor growth. The invention also has applications in assessment of fine structures for a range of industrial purposes such as measurement of material properties in manufacturing or in geology to characterize various types of rock, as well as other uses for which measurement of fine structures/textures is needed.

2. Description of the Related Art

Though fine textural changes in tissue have long been recognized as the earliest markers in a wide range of diseases, robust clinical assessment of fine texture remains elusive, the main difficulty arising from blurring caused by subject motion over the time required for data acquisition.

Early and accurate diagnosis is key to successful disease management. Though clinical imaging provides much information on pathology, many of the tissue changes that occur as a result of disease onset and progression, or as a result of therapy, are on an extremely fine scale, often down to tens of microns. Changes in fine tissue texture have been recognized for many years by diagnosticians, including radiologists and pathologists as the earliest harbinger of a large range of diseases, but in vivo assessment and measurement of fine texture has remained outside the capabilities of current imaging technologies. For instance, differential diagnosis of obstructive lung disease relies on a textural presentation in the lung parenchyma, but the robustness of the Computed Tomography (CT) measure of early stage disease is limited. Trabecular bone microarchitecture, the determinant of fracture risk in aging bone, has also remained elusive due to image blurring from patient motion during Magnetic Resonance (MR) imaging scans. Post processing analysis of MR-images is sometimes used to try to differentiate surface textures in structures such as tumors and white matter. (DRABYCZ, S., et al.; "Image texture characterization using the discrete orthogonal S-transform"; Journal of Digital Imaging, Vol. 22, No 6, 2009. KHIDER, M., et al.; "Classification of trabecular bone texture from MRI and CT scan images by multi-resolution analysis"; 29th Annual International Conference of the IEEE Engineering in Medicine and Biology Society, EMBS 2007.) But post processing analysis is limited in effect as it doesn't deal with the underlying problem that prevents high resolution acquisition of textural information, i.e. subject motion. (MACLAREN, J. et al.; "Measurement and correction of microscopic head motion during magnetic resonance imaging of the brain", PLOS/ONE, Nov. 7, 2012. MACLARAN, J. et al.; "Prospective motion correction in brain imaging: a review; Magnetic Resonance in Medicine, Vol. 69, 2013.)

The main sources of motion affecting MR imaging are cardiac pulsatile motion, respiratory-induced motion and twitching. The first two are quasi-cyclic, the usual approach to which is gating at the slowest phase of motion. However, even with gating, there is sufficient variation between acquisitions to cause loss of spatial phase coherence at the high k-values of interest for texture measurements. This problem is exacerbated by the fact that motion may not be perfectly cyclic, and often originates from combined sources. Twitching is rapid, inducing random displacements, and hence it is not possible to maintain coherence at the high k-values of interest when measuring texture.

While Positron Emission Tomography (PET) provides valuable diagnostic information, it is not capable of resolution below about 5 mm and relies on the use of radioactive tracers for imaging as well as x-ray beams for positioning, raising dose concerns, especially if repeat scanning is needed. (BERRINGTON DE GONZALEZ, A. et al.; "Projected cancer risks from Computed Tomographic scans performed in the United States in 2007"; JAMA Internal Medicine, Vol. 169, No. 22, December 2009.) Further, PET imaging is extremely costly, requiring a nearby cyclotron. CT resolution down to 0.7 mm is possible in theory, though this is obtained at high radiation dose and is subject to reduction by patient motion over the few minute scan time. The non-negligible risk from the associated radiation dose makes CT problematic for longitudinal imaging and limits available resolution. Along with serious dose concerns, digital x-ray resolution is limited because the 2-dimensional image obtained is a composite of the absorption through the entire thickness of tissue presented to the beam. Current clinical diagnostics for the diseases that are the target of the method claimed herein are fraught with difficulties in obtaining sufficient in vivo resolution, or accuracy. In some cases, no definitive diagnostic exists currently. In other pathologies, particularly in breast and liver, diagnosis is dependent on biopsy, with its non-negligible risk of morbidity and even mortality, and which is prone to high read and sampling errors. (WELLER, C; "Cancer detection with MRI as effective as PET-CT scan but with zero radiation risks"; Medical Daily, Feb. 18, 2014.)

Bone health is compromised by aging, by bone cancer, as a side effect of cancer treatments, diabetes, rheumatoid arthritis, and as a result of inadequate nutrition, among other causes. Bone disease affects over ten million people annually in the US alone, adversely affecting their quality of life and reducing life expectancy. For assessment of bone health, the current diagnostic standard is Bone Mineral Density (BMD), as measured by the Dual Energy X-ray Absorptiometry (DEXA) projection technique. This modality yields an areal bone density integrating the attenuation from both cortical and trabecular bone, similar to the imaging mechanism of standard x-ray, but provides only limited information on trabecular architecture within the bone, which is the marker linked most closely to bone strength. (KANIS, J. AND GLUER, C.; "An update on the diagnosis and assessment of osteoporosis with densitometry"; Osteoporosis International, Vol. 11, issue 3, 2000. LEGRAND, E. et al.; "Trabecular bone microarchitecture, bone mineral density, and vertebral fractures in male osteoporosis"; JBMR, Vol. 15, issue 1, 2000.) BMD correlates only loosely with fracture risk. A post-processing technique, TBS (Trabecular Bone Score) attempts to correlate the pixel gray-level variations in the DEXA image, to yield information on bone microarchitecture. A comparison study determined that BMD at hip remains a better predictor of fracture. But, though TBS does not yield a detailed assessment of trabecular architecture. (BOUSSON, V., et al.; "Trabecular Bone Score (TBS): available knowledge, clinical relevance, and future prospects"; Osteoporosis International, Vol. 23, 2012. DEL RIO, et al.; "Is bone microarchitecture status of the spine assessed by TBS related to femoral neck fracture? A Spanish case-control study": Osteoporosis International, Vol. 24, 2013.) TBS is a relatively new technique and is still being evaluated.

Measurement of bone microarchitecture, specifically trabecular spacing and trabecular element thickness, requires resolution on the order of tenths of a millimeter. MRI, ultrasound imaging, CT, and microCT have all been applied to this problem. In MRI, though high contrast between bone and marrow is readily obtained, resolution is limited by patient motion over the long time needed to acquire an image with sufficient resolution to characterize the trabecular network. The finer the texture size of this network, the greater the blurring from motion. An attempt to mitigate the effects of patient motion by looking only at the skeletal extremities, removed from the source of cardiac and respiratory motion sources, has been tried using both MRI and microCT. However, the correlation between bone microarchitecture in the extremities and that in central sites in not known. Further, a large data matrix, hence long acquisition time, is still required to obtain sufficient image information to determine trabecular spacing and element thickness. This long acquisition time results in varying levels of motion-induced blurring, depending on patient compliance—twitching is still a serious problem even when measuring extremities. A proposed MR-based technique, fineSA (JAMES, T., CHASE, D.; "Magnetic field gradient structure characteristic assessment using one dimensional (1D) spatial-frequency distribution analysis"; U.S. Pat. No. 7,932,720 B2; Apr. 26, 2011.), attempts to circumvent the problem of patient motion by acquiring a much smaller data matrix of successive, finely-sampled, one-dimensional, frequency-encoded acquisitions which are subsequently combined to reduce noise. Imaging in this case is reduced to one dimension, reducing the size of the data matrix acquired and, hence, the acquisition time. However, as the gradient encoded echoes, are very low Signal to Noise (SNR), noise averaging is required. Though some resolution advantage is gained by this method relative to 2 and 3-d imaging, the need to acquire many repeat spatially-encoded echoes over several response times (TRs) for signal averaging results in an acquisition time on the order of minutes—too long to provide motion immunity. Thus, resolution improvement obtainable by the technique is limited.

What is needed is an accurate, robust, non-invasive, in vivo measure of trabecular spacing and trabecular element thickness capable of assessing bones in the central skeleton, as these are the key markers for assessing bone health and predicting fracture risk. Until now, no clinical technique has been able to provide this capability.

Fibrotic diseases occur in response to a wide range of biological insults and injury in internal organs, the development of collagen fibers being the body's healing response. The more advanced a fibrotic disease, the higher the density of fibers in the diseased organ. Fibrotic pathology occurs in a large number of diseases, from lung and liver fibrosis, to cardiac and cystic fibrosis, pancreatic fibrosis, muscular dystrophy, bladder and heart diseases, and myelofibrosis, in which fibrotic structures replace bone marrow. Fibrotic development is attendant in several cancers, such as breast cancer. A different pathology development is seen in prostate cancer, where the disease destroys healthy organized fibrous tissue. In all cases, textural spacings highlighted in the tissue change in response to disease progression, as collagen fibers form along underlying tissue structures. In liver disease, the textural wavelength changes as the healthy tissue texture in the liver is replaced by a longer wavelength texture originating from the collagen "decoration" of the lobular structure in the organ. In other organs/diseases, textural change reflects the upset in healthy tissue with development of texture indicative of fibrotic intervention.

To span the range of disease progression in most fibrotic pathologies, evaluation of textural changes from fibrotic development requires resolution on the scale of tenths of a mm. One of the most prevalent of such pathologies, liver disease, is representative of the difficulty of assessing fibrotic structure. Currently, the gold standard for pathology assessment is tissue biopsy—a highly invasive and often painful procedure with a non-negligible morbidity—and mortality—risk (patients need to stay at the hospital for post-biopsy observation for hours to overnight), and one that is prone to sampling errors and large reading variation. (REGEV, A.; "Sampling error and intraobserver variation in liver biopsy in patients with chronic HCV infection"; American Journal of Gastroenterology; 97, 2002. BEDOSSA, P. et al.; "Sampling variability of liver fibrosis in chronic hepatitis C"; Hepatology, Vol. 38, issue 6, 2004. VAN THIEL, D. et al.; "Liver biopsy: Its safety and complications as seen at a liver transplant center"; Transplantation, May 1993.) Ultrasound, another modality often used to assess tissue damage in liver disease, is only able to provide adequate assessment in the later stages of the disease—it is used to diagnose cirrhosis. Magnetic Resonance-based Elastography (MRE), which has been under development for some time for use in assessment of liver disease, is not capable of early-stage assessment—the read errors are too large prior to significant fibrotic invasion (advanced disease). Further, this technique requires expensive additional hardware, the presence of a skilled technician, and takes as much as 20 minutes total set up and scanning time, making it a very costly procedure. The ability to image fibrotic texture directly by MR imaging is compromised both by patient motion over the time necessary to acquire data and by lack of contrast between the fibers and the surrounding tissue. Even acquisition during a single breath hold is severely compromised by cardiac pulsatile motion and noncompliance to breath hold, which results in significant motion at many organs, such as liver and lungs. And SNR is low enough that motion correction by combining reregistered MR-intensity profiles obtained from successive echoes is extremely problematic. Similarly, assessment of the amount of cardiac fibrosis in early stage disease using MRI is seriously hampered by cardiac pulsation over the time of the measurement. As motion is, unlike Gaussian noise, a non-linear effect, it can't be averaged out—there must be sufficient signal level to allow reregistration before averaging for electronic noise-reduction. A more sensitive (higher SNR), non-invasive technique, capable of assessing textural changes throughout the range of fibrotic development, from onset to advanced pathology, is needed to enable diagnosis and monitoring of therapy response.

Onset and progression of a large number of neurologic diseases are associated with changes in repetitive fine neuronal and vascular structures/textures. However, ability to assess such changes in the brain is only available post mortem. Currently, definitive diagnosis of Alzheimer's Disease (AD) is by post mortem histology of brain tissue. AD and other forms of dementia such as Dementia with Lewy Bodies, motor diseases such as Amyotrophic Lateral Sclerosis (ALS), Parkinson's disease, conditions precipitated by Traumatic Brain Injury (TBI) such as Chronic Traumatic Encephalopathy (CTE), as well as those caused by other pathologies or trauma, or conditions that involve damage to brain structures such as Multiple Sclerosis (MS), Cerebrovascular Disease (CVD), and other neurologic diseases, are often only diagnosable in advanced stages by behavioral and memory changes, precluding the ability for early stage intervention. Further, conditions such as epilepsy and autism have been associated with abnormal variations in fine neuronal structures, which, if clinically diagnosable, would allow targeted selection for testing therapy response.

Various in vivo diagnostic techniques are available for AD and other dementias, but none of them are definitive. These techniques range from written diagnostic tests, which are prone to large assessment errors, to PET imaging to assess amyloid plaque density or glucose metabolism (FDG PET). As discussed previously, PET imaging is extremely expensive, cannot provide high resolution, and relies on use of radioisotopes and positioning x-ray beams, complicating approval for longitudinal use due to dose concerns. Further, neither amyloid imaging nor FDG PET has been shown to provide a definitive indication of AD. (MOGHBEL, M. et al. "Amyloid Beta imaging with PET in Alzheimer's disease: is it feasible with current radiotracers and technologies?"; Eur. J. Nucl. Med. Mol. Imaging.)

Use of CSF biomarkers for dementia diagnosis is painful and highly invasive and cannot differentiate signal levels by anatomic position in the brain, as is possible with imaging biomarkers. As various forms of dementia are found to have different spatial/temporal progression through the brain, this is a serious drawback to use of liquid biopsy. Another disease associated with various forms of dementia is CVD (Cerebrovascular Disease), which induces cognitive impairment as a result of reduced blood flow through blocked vessels leading to brain tissue. Something capable of high-resolution assessment of pathology-induced changes in micro-vessels is needed here.

Tissue shrinkage due to atrophy in many forms of dementia including AD is measurable with careful registration of longitudinally-acquired data in MRI, but the disease is advanced by the time this shrinkage is measurable. Early stages of disease are indicated in post mortem histology by degradation in the columnar ordering of cortical neurons, the normal spacing for these columns being on the order of 100 microns in most cortical regions. (CHANCE, S. et al.; "Microanatomical correlates of cognitive ability and decline: normal aging, MCI, and Alzheimer's disease"; Cerebral Cortex, August 2011. E. DI ROSA et al.; "Axon bundle spacing in the anterior cingulate cortex of the human brain"; Journal of Clinical Neuroscience, 15, 2008.) This textural size, and the fact that the cortex is extremely thin, makes speed of acquisition paramount, as even tiny patient motion will make data collection impossible. Assessment of textural changes on the order of tens of microns microns is extremely problematic in vivo, but would, if possible, enable targeting a range of fine textural changes in neuronal disease diagnosis and monitoring, and would play an important role in therapy development.

Another possible neurologic application for the claimed method is to, in vivo, determine the boundaries of the various control regions of the cerebral cortex or the different Brodmann's areas of which these are comprised. Such ability would greatly aid data interpretation in brain function studies, such as those performed using, for example, FMRI (Functional Magnetic Resonance Imaging).

The three classes of diseases listed above, bone disease, fibrotic diseases, and neurologic diseases are not an all-inclusive list. Other disease states in which pathology-induced changes of fine structures occur, for instance angiogenic growth of vasculature surrounding a tumor, or fibrotic development and changes in vasculature and mammary gland ducting in response to breast tumor development, also are pathologies wherein the ability to resolve fine tissue textures would enable early detection of disease, and monitoring of response to therapy.

The ability to measure changes in fine textures would be of great value for disease diagnosis. Non-invasive techniques that do not rely on use of ionizing radiation or radioactive tracers allow the most leeway for early diagnosis and repeat measurement to monitor disease progression and response to therapy. Magnetic Resonance Imaging (MRI), which provides tunable tissue contrast, is just such a non-invasive technique, with no radiation dose concerns. However, in order to circumvent the problem of signal degradation due to patient motion, data must be taken on a time scale not previously possible.

SUMMARY OF THE INVENTION

A method for selective sampling to assess texture using magnetic resonance (MR) is accomplished by exciting a volume of interest. All gradients are then turned off and multiple samples of an RF signal encoded at a specific k-value are recorded in a single TR. In certain embodiments, exciting the volume of interest is accomplished in an exemplary embodiment by transmitting a first RF pulse with a first gradient activated for slice selection, transmitting a second RF pulse with a second gradient activated, said second gradient chosen for slice selective refocusing in a region defined by an intersection of the first slice and a second slice, apply a selected gradient pulse shaped to induce phase wrap to create a spatial encode with resulting pitch corresponding to texture wavelength of the specific k-value and then transmitting a third RF pulse with a third gradient activated. The third gradient is adapted to refocus excitation defining a region defined by the intersection of the first and second slices and this third slice selection. In yet a further embodiment, a selection pulse is issued on a vector combination gradient to alter to a second k-value. The gradient is then again turned off and multiple samples of the RF signal are recorded at the second k-value, while in the same TR. This embodiment may be extended by issuing additional selection gradient pulses for a predetermined plurality of pulses on the vector combination gradient with each pulse selecting a new k-value. With the vector combination gradient turned off after each pulse, multiple samples of the RF signal at the next k-value induced at each negative pulse are recorded while still in the same TR.

An additional embodiment provides for transmitting a refocusing RF pulse with the third gradient activated and then issuing a plurality of selection gradient pulses on the vector combination gradient, each pulse selecting a new k-value. After each pulse of the vector combination gradient, multiple samples of the RF signal at the next k-value induced are recorded, again still in the same TR. This embodiment may be further refined by transmitting a second refocusing RF pulse with the third gradient activated and then issuing a plurality of selecting gradient pulses on the vector combination gradient, with each pulse selecting a new k-value. With the vector combination gradient turned off after each pulse, multiple samples of the RF signal at the next k-value induced at each pulse are recorded.

An additional embodiment provides for recalling the signal multiple times using a GRE (Gradient Recalled Echo), thereby extending the record window to allow acquisition of additional k-value samples.

In an extension of the described embodiments, the number of samples at each new k-value following each of the plurality of pulses on the vector combination gradient is selected based upon expected SNR, pathology, tissue contrast, texture size or texture bandwidth.

Additionally for the embodiments, the volume of interest in the step of exciting a volume of interest is selected using the set of intersecting slice-selective refocusing, selective excitation using phased-array transmit in combination with appropriate gradients, adiabatic pulse excitation to scramble signal from the tissue outside a region of interest, outer volume suppression sequences, and other methods of selectively exciting spins in an internal volume including physically isolating the tissue of interest.

The initial embodiment may be employed wherein the steps of exciting a volume of interest, turning off all gradients and recording samples of an RF signal at a specific k-value are repeated multiple times within the same TR or in succeeding TRs to build a magnitude power spectrum, the specific k-values in each TR independent of intervening motion if constrained within the volume of interest for each TR.

Alternatively, the steps of exciting a volume of interest, turning off all gradients and recording samples of an RF Signal at a specific k-value are repeated multiple times within the same TR or in succeeding TRs with variation of the volume of interest thereby acquiring textural data to assess a textural variation within or across an organ or anatomy.

BRIEF DESCRIPTION OF THE DRAWINGS

The features and advantages of embodiments disclosed herein will be better understood by reference to the following detailed description when considered in connection with the accompanying drawings wherein.

DETAILED DESCRIPTION OF THE INVENTION

Figure 1:
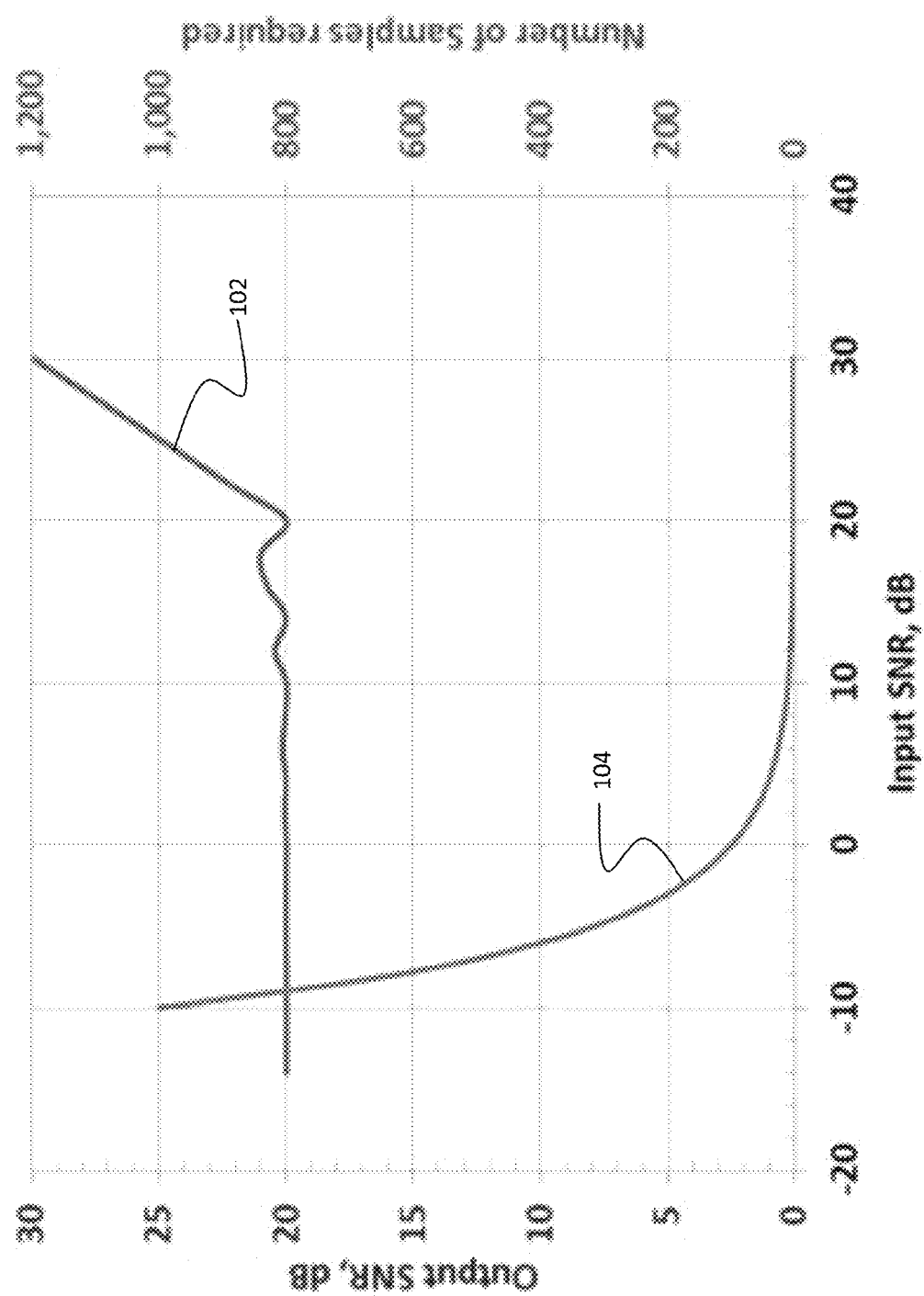
FIG. 1 is a simulation showing the number of data samples required for averaging to achieve an output SNR≥20 dB as a function of input SNR.

The following definition of terms as used herein is provided:

180° inversion pulse RF pulse that inverts the spins in a tissue region to allow refocusing of the MR signal.
180° pulse An RF pulse that tips the net magnetic field vector antiparallel to $B_0$
90° pulse An RF pulse that tips the net magnetic field vector into the transverse plane relative to $B_0$
3T 3 Tesla
A/D Analog to digital converter
AD Alzheimer's Disease
ADC Average diffusion coefficient measured in Diffusion Weighted Imaging
Adiabatic pulse excitation Adiabatic pulses are a class of amplitude- and frequency-modulated RF-pulses that are relatively insensitive to B1 inhomogeneity and frequency offset effects.
AWGN Additive White Gaussian Noise Additive white Gaussian noise (AWGN) is a basic noise model used in Information theory to mimic the effect of many random processes that occur in nature.
Biopsy A biopsy is a sample of tissue extracted from the body in order to examine it more closely.
C/N Contrast to Noise, a measure of image quality based on signal differences between structural elements rather than on overall signal level
CAWGN Complex-valued, additive white Gaussian noise
CBF Cerebral Blood Flow
Chemical shift Small variations in MR resonant frequency due to the different molecular environments of the nuclei contributing to an MR signal.
CJD Creutzfeld-Jakob Disease
Crusher gradients Gradients applied on either side of a 180° RF refocusing slice selection pulse to reduce spurious signals generated by imperfections in the pulse.
CSF Cerebrospinal fluid
DEXA Dual Energy X-ray Absorptiometry is a means of measuring bone mineral density using two different energy x-ray beams.
DSC Dynamic susceptibility contrast
DTI Diffusion Tensor Imaging
DWI Diffusion Weighted Imaging
Echo The RF pulse sequence where a 90° excitation pulse is followed by a 180° refocusing pulse to eliminate field inhomogeneity and chemical shift effects at the echo.

Frequency encodes Frequency-encoding of spatial position in MRI is accomplished through the use of supplemental magnetic fields induced by the machine gradient coils Gaussian noise Gaussian noise is statistical noise having a probability density function (PDF) equal to that of the normal distribution, which is also known as the Gaussian distribution.

Gradient pulse a pulsing of the machine magnetic field gradients to alter the k-value encode Gradient set the set of coils around the bore of an MR scanner used primarily to spatially encode signal or to set a particular phase wrap in a selected direction GRE Gradient Recalled Echo Interleaved acquisition Signal acquisition from a multiplicity of VOIs, successively excited within a single TR Isochromat A microscopic group of spins that resonate at the same frequency.

k-space The 2D or 3D Fourier transform of the MR image.

k-value coefficient The coefficient in a Fourier series or transform reflecting the relative weight of each specific k-value in the series.

k-space The 2D or 3D Fourier transform of the MR image.

k-value One of the points in k-space reflecting the spacing of structural elements in a texture field.

k-value selection pulse The gradient pulse used to select a specific k-value encode along the sampled direction Library of k-space values the net collection of k-space coefficients acquired in a particular region of tissue for tissue characterization Machine gradients the magnetic field gradients imposable through use of the set of gradient coils in an MR scanner MRE Magnetic Resonance Elastography—an imaging technique that measures the stiffness of soft tissues using acoustic shear waves and imaging their propagation using MRI.

MRI Magnetic Resonance Imaging

MS Multiple Sclerosis

Noise floor In signal theory, the noise floor is the measure of the signal created from the sum of all the noise sources and unwanted signals within a measurement system PET Positron Emission Tomography is a functional imaging technique that produces a three-dimensional image of functional processes in the body using a positron-emitting radiotracer.

Phase coherence (spatial) When referring to multiple measurements within a common VOI of a or multiple k-values indicates that the sample has the same position relative to the measurement frame of reference Phase encode A phase encode is used to impart a specific phase angle to a transverse magnetization vector. The specific phase angle depends on the location of the transverse magnetization vector within the phase encoding gradient, the magnitude of the gradient, and the duration of the gradient application.

Phase wrap The helical precession of the phase of the transverse magnetization along a phase encoded sample Pitch with reference to the pitch of a screw, the tightness of the phase wrap along the direction of k-value encode Profile A one dimensional plot of signal intensity RF Radio Frequency electromagnetic signal Semi-crystalline texture a texture exhibiting regular spacing along one or more directions slice (slab) Used interchangeably to indicate a non-zero thickness planar section of the Slice-selective refocusing Refocusing of spins through combination of a slice selective gradient and an RF pulse such that the bandwidth of the RF pulse selects a thickness along the direction of the gradient, and the RF pulse tips the net magnetization vector away from its equilibrium position Only those spins processing at the same frequency as the RF pulse will be affected.

SE Spin Echo

SNR Signal to Noise Ratio

Spoiler gradients see crusher gradients

T2 Defined as a time constant for the decay of transverse magnetization arising from natural interactions at the atomic or molecular levels.

T2* In any real NMR experiment, the transverse magnetization decays much faster than would be predicted by natural atomic and molecular mechanisms; this rate is denoted T2* ("T2-star"). T2* can be considered an "observed" or "effective" T2, whereas the first T2 can be considered the "natural" or "true" T2 of the tissue being imaged. T2* is always less than or equal to T2.

TBS Trabecular Bone Score is a technique that looks for texture patterns in the DEXA signal for correlation with bone microarchitecture for assessing bone health TE Spin Echo sequences have two parameters: Echo Time (TE) is the time between the 90° RF pulse and MR signal sampling, corresponding to maximum of echo. The 180° RF pulse is applied at time TE/2. Repetition Time is the time between 2 excitations pulses (time between two 90° RF pulses).

Textural frequency the number of texture wavelength repeats per unit length in a texture Texture wavelength the characteristic spacing between structural elements in a texture TR Spin Echo sequences have two parameters: Echo Time (TE) is the time between the 90° RF pulse and MR signal sampling, corresponding to maximum of echo. The 180° RF pulse is applied at time TE/2. Repetition Time is the time between 2 excitations pulses (time between two 90° RF pulses).

Vector combination gradient A magnetic gradient resulting from any vector combination of the gradient coil set VOI Volume of Interest Windowing function In signal processing, a window function (also known as an apodization function or tapering function) is a mathematical function that is zero-valued outside of some chosen interval x-ray diffraction X-ray diffraction is a tool used for identifying the atomic and molecular structure of a crystal The embodiments disclosed herein provide an MR-based technique that enables in vivo, non-invasive, high-resolution measurement and assessment of fine biologic textures, enabling monitoring of texture formation and/or change in response to disease onset and progression in a range of pathologies. This same method can be applied to fine-texture characterization in other biologic and physical systems. It enables MR-based resolution of fine textures to a size scale previously unattainable in in vivo imaging. The method, while described herein with respect to biological systems for examination of tissue, is equally applicable for assessment of fine structures in a range of industrial purposes such as measurement of material properties in manufacturing or in geology to characterize various types of rock, as well as other uses for which measurement of fine structures/textures is needed.

The method claimed herein achieves this significant improvement in in vivo resolution of fine texture by acquiring the requisite data fast enough that the effect of subject motion, the factor that limits MRI resolution, becomes negligible. This fast acquisition is achieved by acquiring data incrementally—at a single location, orientation and at one, or a select set, of k-values at a time—within one TR. After applying an encoding gradient to select the k-value of interest, data is acquired with the gradient switched off, allowing multiple acquisition repeats of the encoded k-value for subsequent averaging to reduce electronic noise, thus enabling robust measure of individual k-values before motion blurring can occur. To build up measurements on a larger set of selected k-values present within the tissue, or towards development of a continuous spectrum of textural spacings within the tissue, the acquisition TR can be repeated as many times as necessary, changing the encode as needed to span the desired extent of real and of k-space required. The set of one or more k-values output from each TR are now high SNR due to the ability to average repeats without motion effects, and since the measure of interest is textural spacing, and not development of an image, the lack of phase coherence between TRs is of no concern.

In its simplest form the method claimed herein consists of acquiring MR signal from within an inner volume to encompass a specific tissue region of interest, such as a lesion, an organ, a location in an organ, a specific region of bone, or a number of regions in a diseased organ for sampling. This inner volume may be excited by one of a number of methods, including but not limited to: intersecting slice-selective refocusing, selective excitation using phased-array transmit in combination with appropriate gradients, adiabatic pulse excitation to scramble signal from the tissue outside the region of interest, outer volume suppression sequences, and other methods of selectively exciting spins in an internal volume including physically isolating the tissue of interest, to name a few, After definition of a volume of interest (VOI), the gradient is turned off, and multiple samples of signal centered at a specific k-value, the spread of which is defined by receiver BW and sampling length, are acquired. This measurement is repeated only in specified directions within the VOI rather than trying to map all of k-space, as is required to generate an image. One or more samples of a particular k-value are acquired within an acquisition block during a single TR and the k-value subsequently incremented or decremented, allowing further multiple samples of other k-values as desired during the same TR. This method allows multiple sampling of each k-value of interest over a time period of milliseconds, providing immunity to subject motion. The process can then be repeated in further TRs, the requirement on motion between k-value acquisitions being only that the VOI remain within the tissue region of interest. Build up of a magnitude spectrum of spatial frequencies may be accomplished without the need to acquire it in a spatially coherent manner. Because the quantities of interest are the relative intensities of the various k-values (textural spacings) present in the sample volume, as long as the acquisition volume remains within a representative sample of tissue, any motion between the blocks does not compromise the measurement. In the case where motion of sufficiently large magnitude that the internally excited volume could move into other tissue volumes over the course of building up a spectrum of k-values contained in the tissue, use of fairly robust, real-time piloting and acquisition algorithms can be used for gross repositioning of the internal selectively excited volume and for rejecting data sets that have failed to stay in the proper tissue.

Repositioning the VOI to allow sampling of texture at multiple positions within or across an organ or anatomy allows determination of the variation in pathology through the organ. The data acquired can, with reference to positioning images, be mapped spatially. Either the VOI can be moved in successive TRs or interleaved acquisition done within a single TR by exciting additional volumes during the time that the signal is recovering in advance of the next TR. The requirement is that successive VOIs be excited in new tissue, that does not overlap the previous slice selects. Spatial variation of pathology can be determined by this method. This can also be used to monitor temporal progression of a pathology through an organ if the measure is repeated longitudinally.

Tailoring the pulse sequence to pre-wind phase in the sample volume positions the highest k-values of interest at the echo peak where the signal is strongest, providing best SNR measurement.

Sampling of k-values along multiple directions at varying angles and along varying paths, either rectilinear or curved, within the volume under study can yield important information on texture, especially textures with semi-ordered structure in specific directions, such as neuronal minicolumns. Measurement of the k-values associated with columnar spacing is extremely sensitive to alignment of the sampling path, as slight variations in sampling direction on either side of perpendicular show a rapid drop off in signal magnitude for that k-value. Rocking the acquisition path on either side of the signal maximum can yield a measure of pathology-induced randomness which is indicated by the width of the peak.

With the gradient switched off for data acquisition, tuning the bandwidth to particular chemical species can enhance structural information when the chemical composition of the structure under study is known.

The method claimed herein can be used in conjunction with time-dependent contrast schemes that target blood flow. Some of these contrast techniques are Blood Oxygenation Level Dependent (BOLD) imaging, Arterial Spin Labeling (ASL) imaging, and Dynamic Susceptibility Contrast (DSC) imaging. As these methods use various techniques to highlight vasculature, changes in the texture of the vasculature associated with many pathologies, including CVD (cerebrovascular disease) and tumor growth can be measured.

The method claimed herein can also be used in conjunction with other MR-based measurement techniques, including DWI and DTI, to provide front end information toward parameter selection for the diffusion techniques as well as correlation with their measurements of tissue health.

The rapid repeat measurement of a single k-value, with the total time to acquire a block being on the order of a msec, reduces patient and machine motion-induced blurring to a negligible level, enabling robust assessment of fine textures previously not accessible in vivo. (For comparison, standard MR image acquisition times are much longer in duration over which patients are asked to remain completely stationary.) The SNR of each k-value measured is significantly improved through combination of the individual samples at each k-value within a block; this averaging can now can be done without concern for subject motion, which is eliminated due to the rapid sequential acquisition of the individual samples in the block.

This significant improvement in SNR is made possible because the method claimed herein focuses on acquiring only the k-values of interest for determination of fine texture pathology signatures rather than on acquisition of the large number of entire spatially-encoded echoes required for image formation. The significantly reduced data matrix enables the increased number of repeats at the targeted k-values, and hence significant improvement in SNR.

Energy density within a range of textural spacings is proportional to textural wavelength, or inversely to k-value—i.e. the higher the k-value, the lower the associated signal intensity. The fast acquisition enabled through use of the method claimed herein, enables tailoring the number of acquisition repetitions at a particular k-value to acquire k-values for which there is low signal first, before $T_2$ and $T_2^*$ effects have degraded signal amplitude. In this way, the SNR of each repeat to be averaged for noise cancellation (or spatial-phase-corrected before combining it with the measurements of k-value from subsequent TRs) will be above this threshold. It does not matter that there is motion between acquisition cycles at different k-values as long as each acquisition lies within the tissue volume of interest (VOI). As the claimed method targets only assessment of pathology-induced changes in tissue texture, there is no requirement for phase coherence over an entire cycle of data acquisition, as is required in imaging.

Several benefits result from acquiring data after the gradient is switched off for single-k-value sampling in a reduced volume (the VOI). By proper pulse sequencing, the echo record window can be designed such that recording begins with the highest k-values of interest, as signal level is highest at the echo peak. This enables recording of fine structures currently unachievable with in vivo MR imaging.

Additionally, T2* is longer with the gradient off, so SNR is improved by the longer acquisition times possible This allows acquisition of an increased number of samples, N.

Coil combination is also simplified by having higher SNR for each k-value, hence providing a significant improvement in overall SNR. This is especially beneficial as the trend in MRI is towards coil arrays composed of many small element coils. As the acquisition volumes targeted in the method claimed herein are small, correction for phase across the sample volume is not needed. Only one phase and gain value for each coil is needed for combining the multiple element channels. These can be combined using the Maximal Ratio Combining (MRC) method, which weights the coil with the highest SNR most heavily, or other multi-signal combination methods. (Phase and gain for the elements of a given coil array can be determined once from a phantom and applied to patient data.)

Signal acquisition and data sampling in a standard MRI scan is done by acquiring complex-valued samples of multiple echoes, while applying a gradient sequence concurrently, as well as in sequence with the echoes. Imaging relies on frequency encode for one of the dimensions because this allows a line in k-space to be acquired with each phase encode rather than a single point. For 3-dimensional imaging, two dimensions in k-space normally rely on phase encode to generate the targeted filling of k-space, with the third dimension frequency-encoded. Phase encode acquisition in imaging usually entails acquisition of on the order of 256 k-values in each of the phase-encode directions, hence is is a relatively slow process. Clinical MRI scans take on the order of 10-15 minutes to generate an image. The aim in image construction is to acquire sufficient k-space coverage to fill out all the coefficients in the 2 or 3-dimensional Fourier series, which is why in standard MR resolution is limited by subject motion.

The method claimed herein is in direct contrast to standard MR data acquisition, with its focus on image generation. Image formation is plagued by blurring resulting from subject motion over the long time necessary to acquire the large data matrix required. Since the target of the method claimed herein is texture rather than image, the only requirement on subject motion is that the sampled volume remain within a region of similar tissue properties over the course of acquiring data. This is a much less stringent and easy to achieve target than the requirement of structural phase coherence, as the scale of the allowable motion is then large enough, and of a temporal order, to be easily correctable by real-time motion assessment and correction techniques. The speed of acquisition for the method claimed herein is such that, in most cases, real-time motion correction may not be necessary at all. While other methods have focused on post-processing of images to try to extract textural measures, the method claimed herein eliminates the need for image generation, focusing instead on directly measuring texture, hence enabling a more sensitive and robust measure.

Frequently, k-space sampling is considered synonymous with sampling of an echo in the presence of a gradient set. In the method claimed herein, the approach to k-space filling is to acquire only the set of k-values needed for texture evaluation in the targeted pathology, with data acquired after the gradient is switched off. This method enables such rapid acquisition of single-k-value repeats for averaging for noise reduction that subject motion does not degrade the data.

Along with the huge improvement in SNR that arises from sampling k-values individually, with many repeats of a select set of k-values acquired in a single TR, acquisition after the gradient is switched off allows further significant improvement in SNR and hence, increase in measurement robustness. This is explained in the following discussion.

MR echo sampling provides specific samples vs. time of a time-dependent echo. The echo is comprised by the gradients applied concurrently (for the frequency-encode axis) and prior to (for a phase encode axis), but also contains the isochromats associated with the different chemical species of the sample, as well as the envelope (T2 & T2*) associated with spin-spin interactions.

Conventional frequency-encoded spin acquisitions impose a time-varying gradient upon the sample, which effectively travels in k-space along a pre-defined path. For rectilinear sampling, the path is along a straight line.

Frequency encodes generate only one measurement at a given k-value—at a given point in time, the acquired sample of the echo represents the one value which corresponds to the Fourier coefficient at a specific k-space location. The next echo sample represents the value at a different k-space location, the next k-value dependent on the slope of the gradient applied concurrently. As long as there is sufficient signal at the corresponding k-value, this approach works well. However, in cases where the signal of interest is near or even below the noise floor, usually additional samples and subsequent post-processing will be required.

One way to reduce the noise floor in a frequency-encoded gradient read-out is to reduce the gradient strength and lower the receiver bandwidth. Decreasing the receiver bandwidth will indeed decrease the noise level, and improve lower signal level detection (proportional to the term $k_B$ TB, with $k_B$ corresponding to Boltzmann's constant, T corresponding to Temperature in Kelvin, and B is the receiver bandwidth in Hz.) However, this comes at the expense of larger chemical shift artifacts.

Chemical shift artifacts arise as a consequence of the different isochromats associated with different chemical species within the biological sample. In a frequency-encoded k-space read-out, those chemical species which resonate at a slightly higher frequency will appear to be displaced from their actual location in image space towards the direction of increasing frequency. If the spatial frequency encoding gradient is shallow, the apparent displacement can be quite large.

As such, to minimize chemical shift artifacts, the gradient slope is typically made as steep as possible to minimize the apparent shift to within a narrow range (i.e. within 1 or two pixels in the image domain). However, this then requires a larger receiver bandwidth to accommodate the larger frequency range. This in turn increases the overall noise floor at a level proportional to the receive bandwidth.

The conclusion is that frequency readouts generally force a trade-off between gradient strength, noise level, and chemical shift artifacts.

A common technique for noise reduction in signal acquisition is through repeat sampling of a signal and subsequent combination of the multiple measurements. For linear noise sources, such as Gaussian noise, this technique improves SNR through cancellation of the random noise on the signal, the cancellation effect increasing with the number of samples, N.

Noise reduction by this cancellation technique works for static subjects. However, motion-induced blurring is a non-linear effect, so signal combining for which the individual measurements have shifted through large spatial phase angles (relative to the textural/structural wavelengths under study) does not lead to an improved SNR. A fairly standard technique to correct for motion is to look at the MR intensity data in real space and reregister successive traces/images to each other to maximize overlap. It is assumed that, as with the reduction in white noise, linear combination of these reregistered signals will result in reduction of the blurring caused by the motion. However, this only works if the SNR on each individual acquisition is high enough. Reregistering low SNR samples results in a high variance in the estimated position. Threshold theory defines that combining reregistered signals with non-linear blurring, when the original signals are below a certain noise threshold, only increases signal error.

The nonlinearity introduced by subject motion increases at higher k-values, since the motion-induced textural phase shift increases with k—i.e. as the size of the structures of interest decrease, the adverse consequence of motion become more acute. This implies that the multiple samples to be combined need to be derived from the same acquisition sequence, acquired in a sufficiently short time span, to ensure there is negligible motion between samples.

The Cramér-Rao Lower Bound provides insight into the number of samples that are required for a lower bound on the residual variance of an estimate, i.e. the SNR vs. number of samples, in Additive White Gaussian Noise (AWGN). For low source SNRs in AWGN, one needs a large number of samples to average in order to obtain a usable SNR. The primary assumption is that multiple acquisitions can be taken, then averaged to achieve the higher SNR. (CRAMÉR, H.; "Mathematical Methods of Statistics"; Princeton University Press, 1946. RAO, C. R., "Information and the accuracy attainable in the estimation of statistical parameters"; Bulletin of the Calcutta Mathematical Society 37, 1945.)

Referring to the drawings, the graph in FIG. 1 comparing output SNR shown in trace 102 with number of samples required shown in trace 104 demonstrates that, for high input SNRs, a single sample is sufficient to yield a low noise measure. For lower SNRs, multiple samples are required to "average out" the noise contribution. The ability to combine the samples explicitly assumes that the underlying signal of interest is relatively constant during the multiple sample acquisition process (i.e. the only component which changes is the noise).

Figure 2:
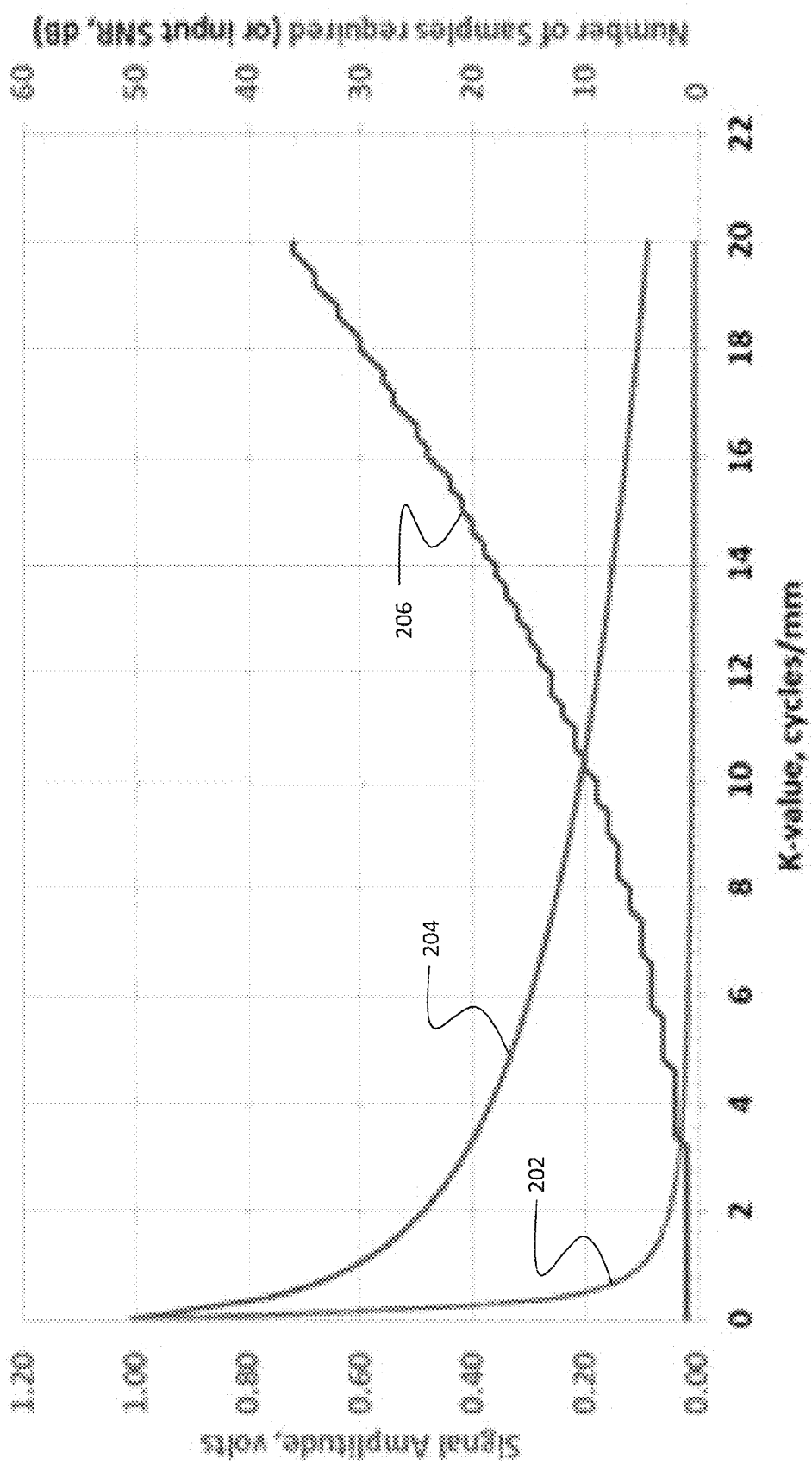
FIG. 2 is a simulation showing the number of data samples needed for averaging to achieve a SNR≥20 db as a function of location in k-space.

The graph in FIG. 2 is a simulation with signal model, trace 202, providing an input SNR, trace 204, showing number of samples of k-value, trace 206, needed to yield a SNR of 20 dB as a function of location in k-space, given an input noise level of 3 mV rms. Since spectral energy density is generally proportional to $k^{-1}$, to maintain adequate SNR a larger number of input samples is required at higher spatial frequencies (higher k-values). The noise level for the simulation is adjusted for ~10 dB SNR at k=2 cycles/mm ($\lambda$=500 μm).

As pointed out above, this type of averaging is possible for purely static samples with no displacement or deformation of the targeted tissue occurring over the temporal span of data acquisition. However, for in vivo applications, natural motion occurs even if the patient is compliant. As the texture spacing of interest decreases, the adverse consequences of motion become more acute. More to the point, this type of averaging is based upon the assumption that the underlying signal is the same across acquisitions, and that only the zero-mean, complex-valued, additive, white Gaussian noise (CAWGN) changes. If the signal itself changes, the result will be an average, not only of the noise, but also of the N different versions of the underlying signal, which really doesn't improve SNR.

Using low SNR samples to estimate and correct for motion will result in a high variance of the estimated position. This in turn yields a large variance in the "corrected" acquisitions and does not yield the anticipated increase in SNR when these acquisitions are averaged. This implies that the multiple samples need to be derived from the same acquisition sequence, where motion between samples is extremely small. This is enabled by the method claimed herein.

The issue becomes more acute with shorter structural wavelengths. Consider two acquisitions, noise-free for the moment, one of which has been displaced by an amount d. For a given k-value, an attempt to average them produces:

$$Y(2\pi k) := S(2\pi k)[1+e^{-j2\pi kd}]/2 \tag{0.1}$$

Where $S(2\pi k)$ the complex-valued signal, and $Y(2\pi k)$ represents the average of the two acquisitions.

This can be expressed as:

$$Y(2\pi k) := S(2\pi k)e^{-j\pi kd}\cos(\pi kd) \tag{0.2}$$

Which shows both a magnitude attenuation and phase shift, due to the displacement d. Limiting the magnitude attenuation to a floor value a, where 0<a<1, limits d to:

$$|d| \leq \frac{\cos^{-1}(a)}{\pi k} \tag{0.3}$$

This shows that, for a given magnitude error, the allowable displacement decreases with increasing values of k. This is because, the smaller the textural spacing of interest, the less motion can be tolerated over the course of data acquisition.

To deal with this problem, an alternate approach is taken in the method claimed herein, which is to dispense with the frequency-encoded readout and to sample specific k-space points, acquiring one or multiple measurements at each k-value of interest at a single spatial location and orientation at a time.

Within a given acquisition in standard MR practice, there are M samples which are acquired of the echo. Instead of acquiring a sample at each k-value, N≤M of those samples could be used for estimation of the (complex-valued) underlying signal value at a specific k-value. Multiple samples within an acquisition can be combined with much less concern of movement than across acquisitions because they are much closer in time.

If the entire echo is used to measure one k-value, the receive bandwidth can be adjusted so as to pass the most abundant resonant peaks in the underlying NMR spectrum, and attenuate frequencies above them.

Taking a straight MRS spectrum (no structural phase encodes), would yield a spectrum consisting primarily of peaks corresponding to $H_2O$ (with a chemical shift of $\delta$=4.7 ppm), as well as Carbon-Hydrogen bonds which occur in fat (e.g. CH3, CH2, CH═CH, etc.), each with a different chemical shift ranging from 0.9-5.7 ppm, with the most abundant resonance coming from CH2 in the aliphatic chain which occurs at δ=1.3 ppm.

Assuming use of a 3T machine, since the Gyromagnetic ratio of Hydrogen is γ=42.576 MHz/T, the chemical shift values are in the range of 166 Hz (for CH2) to 600.3 Hz (for H2O). As long as a (single sided) receiver bandwidth in excess of 600.3 Hz is used, the H2O peak will pass. Assuming baseband sampling, this implies a sampling rate >1.2 kHz (note, if complex base-band sampling is used, this could theoretically be reduced by about ½) The point here is that a narrow bandwidth can be used by this method, and sample rates on the order of 800 µs. Noise on the signal is thereby reduced and multiple repeats of the k-value acquisition data are acquired in milliseconds, thereby making the acquired data immune to patient motion. For comparison, a single imaging acquisition is made with a TE of ~30 ms, and TR on the order of 500 ms-2000 ms. To acquire the repeats necessary for signal averaging can take minutes—a temporal range wherein respiratory, cardiac, and twitching motion limits resolution through motion-induced blurring. The claimed method enables acquisition of values in regions of k-space which have very low signal levels, such as would be found for higher k-values (shorter textural-wavelengths)—the fine texture range that has hitherto remained elusive.

To maximize the signal, the non-zero frequencies of abundance are selected. In general, this does not correspond to a mere averaging of all of the samples acquired. Instead it is akin to a matched filter which is "tuned" to the frequency of interest, corresponding to the specific chemical species of interest.

As a side note, the full NMR spectrum may be extracted (without any phase encoding gradients: just volume selection) to obtain a baseline of the underlying signal strength (and associated frequencies), which in turn will be spatially modulated, providing insight into textural wavelengths through knowledge of the chemical species expected in the textural elements under study.

The isochromats of interest can be extracted by acquiring N samples of the echo, then taking the Fourier transform. Since the echo is being played out with no gradient, the strength of the resulting signal at the Isochromat of interest will correspond to the (complex-valued) k-value coefficient of interest.

Given the goal is to extract the relative magnitude of textural wavelengths, just the magnitude vs. textural wavelength measurement is the required information. However, in order to extract sufficient signal strength and differentiate it from the underlying noise floor, the complex phasor values must be preserved until the end.

The relationship between the noise floor, the signal strength (at a specific isochromat where there is an abundance of chemical species), the number of samples required, and the max tolerated error can be approximated as $$N \geq \frac{\sigma^2}{|A|^2 \varepsilon^2} \qquad (0.4)$$

Where $\sigma^2$ represents the noise variance, $|A|^2$ represents the squared magnitude of the isochromat(s) of interest, and $0 < \varepsilon < 1$ represents the allowable error of the estimate. Further assuming that the noise is mostly sourced from the biological sample, this can be further approximated as:

$$N \geq \frac{NF_{eff} \cdot k_B TB}{|A|^2 \varepsilon^2} \qquad (0.5)$$

Where $NF_{eff}$ is the effective noise figure of the receiver, $k_B$ is Boltzmann's constant, T is the temperature in Kelvin of the biological sample, and B is the receiver bandwidth. In this case, N can be used as a guide to the number of samples that need to be acquired within a given acquisition in order to create a reasonable estimate.

If the number of samples required exceeds the number available in one acquisition, combination of measurements from a single acquisition may be needed to maximize the signal, prior to spatial reregistration between acquisitions. A reasonable estimate and displacement correction between the two or more acquisition sets is needed. Combination of measurements at a single k-value from a single TR block can now be used to boost the SNR such that reregistration between successive TRs has a much greater chance of success.

While the entire set of samples acquired in an echo or entire TR could be allocated to the estimate of one coefficient in k-space, if acceptable values can be estimated using fewer than the maximum number of echo samples, it opens up the possibility of being able to acquire more than one coefficient in k-space within a specific echo or TR.

Figure 3:
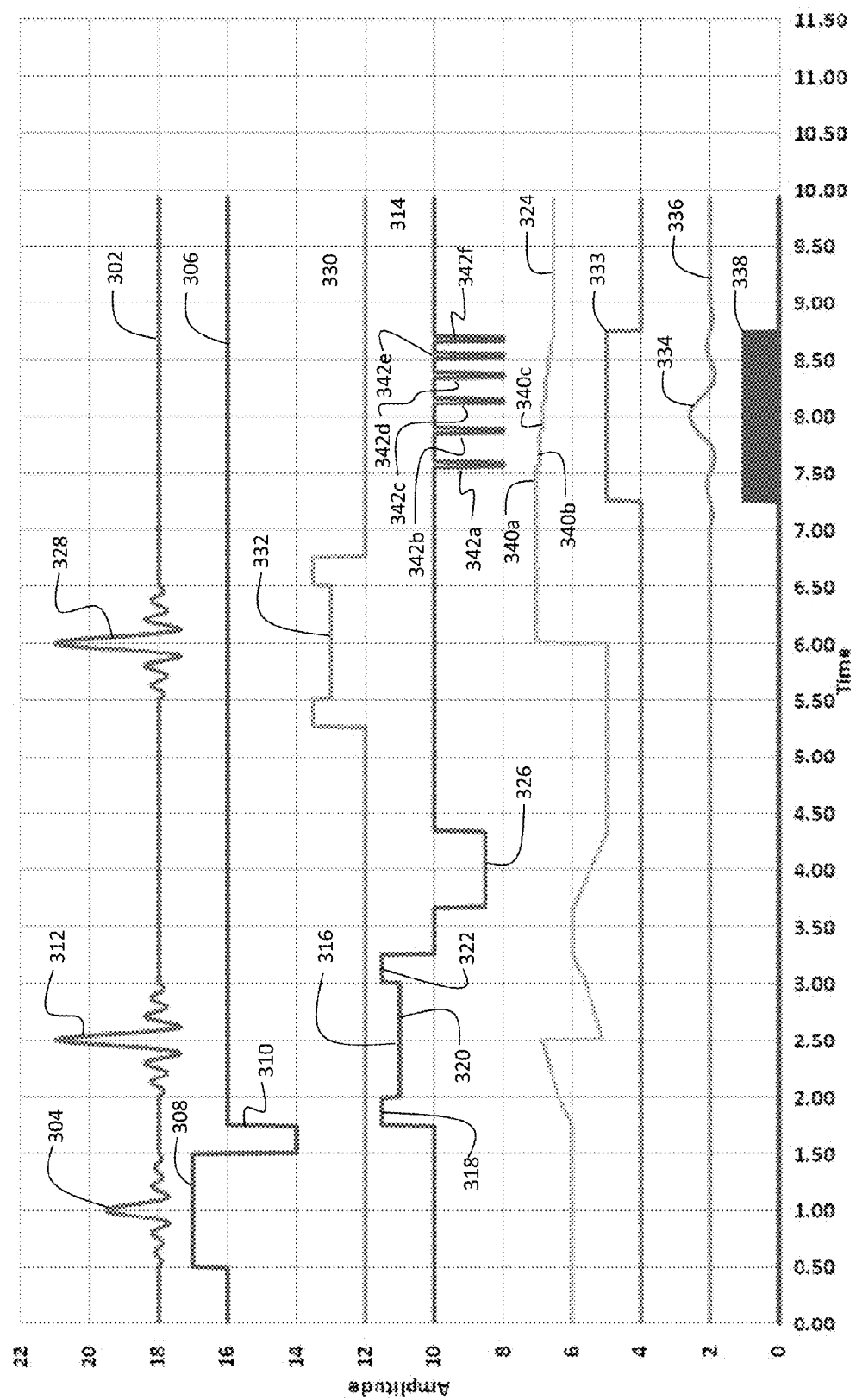
FIG. 3 is an example timing diagram of a pulse sequence for the claimed method showing the timing of a single TR.

FIG. 3 shows an example timing diagram for a pulse sequence for data acquisition using the method claimed herein. RF pulses included in trace 302 are employed to excite selected volumes of the tissue under investigation, as in typical MR imaging. A first RF pulse, 304, is transmitted coincidentally with a gradient pulse 308 on the a first magnetic field gradient, represented in trace 306. This excites a single slice, or slab, of tissue the positioning of which is dependent on the orientation and magnitude of the first gradient, and the frequencies contained in the RF pulse. The negative gradient pulse, pulse 310, rephases the excitation within the defined thickness of the slice or slab.

A second RF pulse 312, at twice the magnitude of first RF pulse 304, is transmitted coincidentally with gradient pulse 316, on a second gradient, represented in trace 314, exciting a slice-selective refocus of spins, this second tissue slice intersecting with the first. (As this second RF pulse 312 tips the net magnetic vector to antiparallel to $B_0$, it results in inversion of spins and subsequent refocusing, thus leading to a signal echo at a time after the 180 degree RF pulse equivalent to the time between the 90° and 180° RF pulses.) An initial higher value gradient pulse, 318, at the start of gradient pulse 316 is a crusher, or "spoiler" gradient, designed to induce a large phase wrap across the tissue volume. A similar gradient pulse, 322, at the trailing end of pulse 316, as it comes after the 180 degree RF inversion pulse, unwinds this phase wrap. In this way, any excitation that is not present prior to the 180 degree RF pulse, such as excitations from imperfections in the 180 pulse itself, will not have this pre-encode so will not be refocused by the second crusher, hence will not contribute to the signal. In summary, the second RF pulse, in combination with the applied second gradient, provides slice selective refocusing of the signal in a region defined by the intersection of the first slice and the second slice set by this second gradient.

An encoding gradient pulse 326, on trace 314, sets an initial phase wrap, hence k-value encode, along the direction of gradient pulse 326. In general, the k-value encode can be oriented in any direction, by vector combination of the machine gradients but for ease of visualization is represented as on the second gradient.

A refocusing third RF pulse 328, applied in combination with gradient pulse 332 on a third gradient, represented by trace 330, defines a third intersecting slice selective refocus to define the VOI. Gradient pulse 332 again employs crusher gradients.

The negative prephasing gradient pulse 326 winds up phase such that, at the signal echo following the second 180° RF pulse, signal acquisition starts at high k-value, which may then be subsequently decremented (or incremented or varied in orientation) for further acquisitions, as will be described below. As energy density in the signal is generally proportional to $k^{-1}$, this method ensures k-values with lower SNR are acquired first, before $T_2$ effects have caused much overall signal reduction.

With all gradients off, a receive gate 333 is opened to receive the RF signal, which is shown in FIG. 3 as pulse 334 on trace 336. The RF signal in trace 336 is a representation showing only the signal present in the receive gate window without showing the actual details of the RF signal outside the window. Sampling occurs as represented by trace 338 beginning with the initial k-value, 340a, seen on trace 324. Note that, at the scale of the drawing, the sampling rate is high enough that the individual triggers of the analog to digital converter (A/D) have merged together in trace 338. (The expanded time scale in FIG. 4 described below shows the individual A/D triggers.)

In regions of k-space where the corresponding coefficients are sufficiently large that they can be well-estimated using a small subset of the samples of one echo, acquisition of another k-value, obtained by applying a gradient pulse 342a shown on trace 314, to select a new k-value, during the time the echo is being recorded, is accomplished. After a suitable settling time, another set of samples of the echo (now derived from the new k-value coefficient) can be collected. This process can be repeated, acquiring multiple samples at each of a select set of k-values within one TR. A plurality of samples are taken at the initial k-value 340a. A k-value selection gradient pulse 342a is then applied and the resultant k-value 340b is sampled. (Though shown in the figure as a negative pulse on the second gradient, decrementing the k-value, in practice this pulse and subsequent k-value gradient pulses can be designed through any vector combination of gradients to select any k-value or orientation.) Similarly, the k-value selection gradient pulse 342b, selects a third k-value 340c which is sampled by the A/D. Each gradient pulse changes the phase wrap, selecting a new k-value. Application of a k-value selection gradient pulse (342c-342f) followed by multiple sampling of the resultant k-value coefficient is repeated as many times as desired. While data is being acquired throughout, the samples of interest are acquired when all gradients are off. The gradient orientations for slice and k-value select may be coincident with the machine gradients, which are aligned to lie coincident or orthogonal to the $B_0$ field. Alternatively, the acquisition directions and k-value encodes may be selected using gradients that are a vector combination of all three machine-gradient axes.

In the circumstance where it is desired to measure a low SNR k-value the prewinding encoding gradient pulse can be set such that the first k-value to be measured is the desired low SNR k-value. Alternatively, the prewinding gradient pulse can be set to zero so that the first k-value measured is k0. A measurement of k0 may be desired for the purpose of determining the systems receiver sensitivity to the particular VOI, determining the relative prevalence of isochromats (e.g., water vs. lipids) irrespective of texture in the VOI, or for the purpose of establishing a reference value for normalization of the other k-values measured in a VOI or for comparison with k-values from other VOI. Furthermore a strategy for gathering a specified set of k-values for a VOI may include measuring the low SNR k-values (typically the higher k-values) in a first set of multiple TR and then measuring k0 and other higher SNR k-values in other TRs while remaining in the same VOI.

As is shown diagrammatically in FIG. 3, the signal magnitude reaches a maximum at the time of the spin echo. It is also shown diagrammatically that the signal magnitude is varying throughout the acquisition of the multiple RF measurements of a k-value and more so between successive blocks of measurements of k-values. Alignment in time of the measurement of the low SNR k-values with the highest echo signal enhances the SNR of the k-value measurement, alternatively alignment of higher SNR k-values with lower echo signal magnitude allows gathering additional useful k-value acquisitions during the echo.

Figure 4:
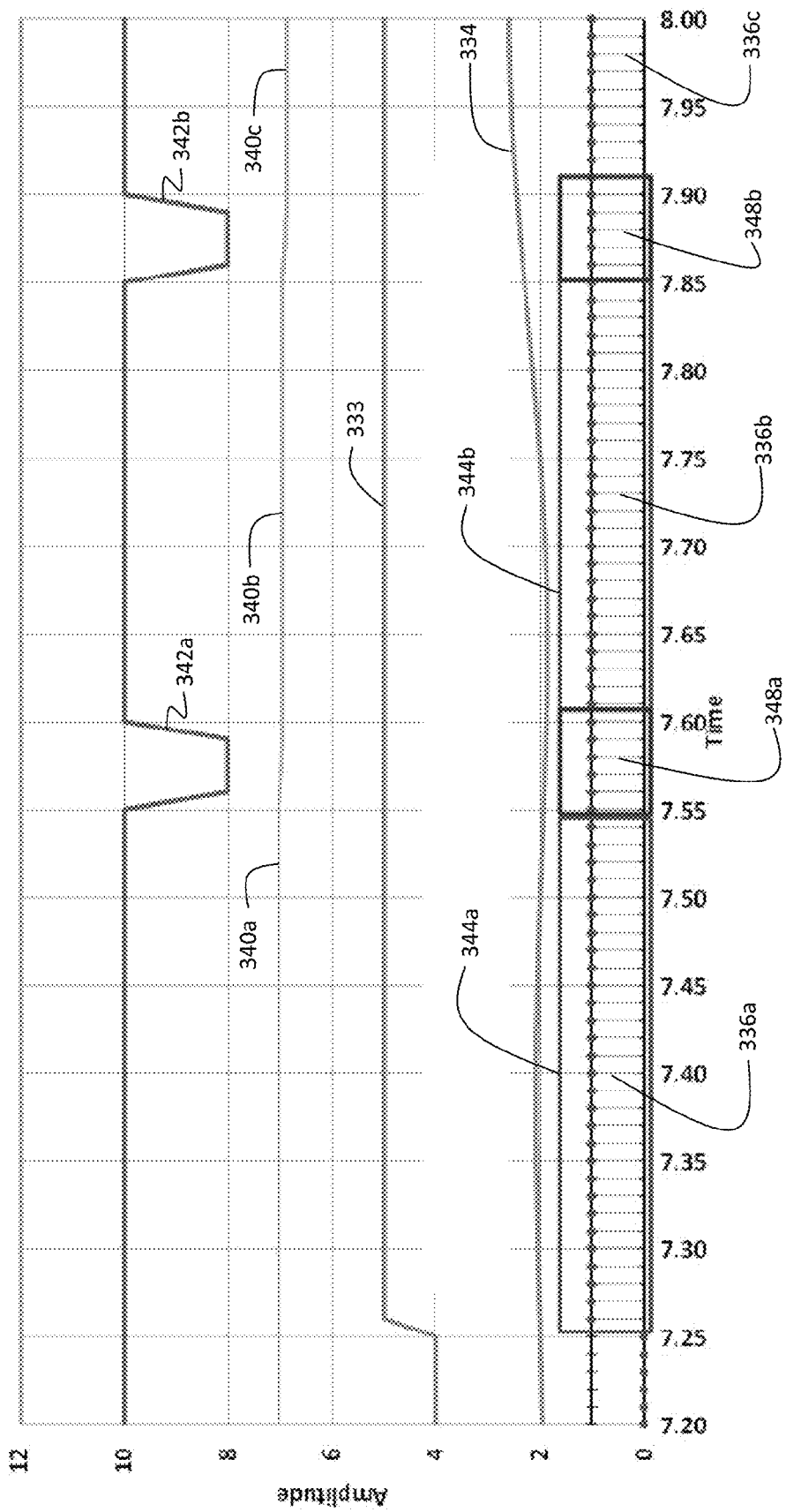
FIG. 4 is a close-up of the example timing diagram of FIG. 3.

FIG. 4 shows a close-up of the pulse sequence of FIG. 3 during the initial portion of the RF sampling window 338 between 7.25 and 8.00 msec. Multiple samples of the same k-value, taken in rapid succession with all gradients off, provide the input for signal averaging to reduce AWGN when SNR is low. In a first block 344a of the sampling window 338, multiple samples 346a are taken of the first k-value 340a. During application of the k-value selection gradient pulse 342a, transition samples 348a are taken. When the k-value selection gradient is switched off, multiple samples 346b are taken at the second k-value 340b. Application of k-value selection gradient pulse 342b then occurs with associated transition samples 348b, and subsequent acquisition of samples 346c of the third k-value 340c after the gradients are switched off. The underlying signal is minimally impacted by motion due to the very short time window used to acquire data at each given k-value. Since the data is acquired with gradients off, there is no issue with chemical shift and the effective $T_2^*$ is longer, boosting the signal value.

The sampled values of the echo, acquired while the k-value selection gradient pulse is ramped up, held steady, and then ramped down to zero, will necessarily be influenced by the applied gradient. These transition samples may provide other interesting information, but are not used in the consideration of a straight measurement of the k-value coefficient; only those samples which are recorded when there is no gradient currently active are used for this.

Figure 5:
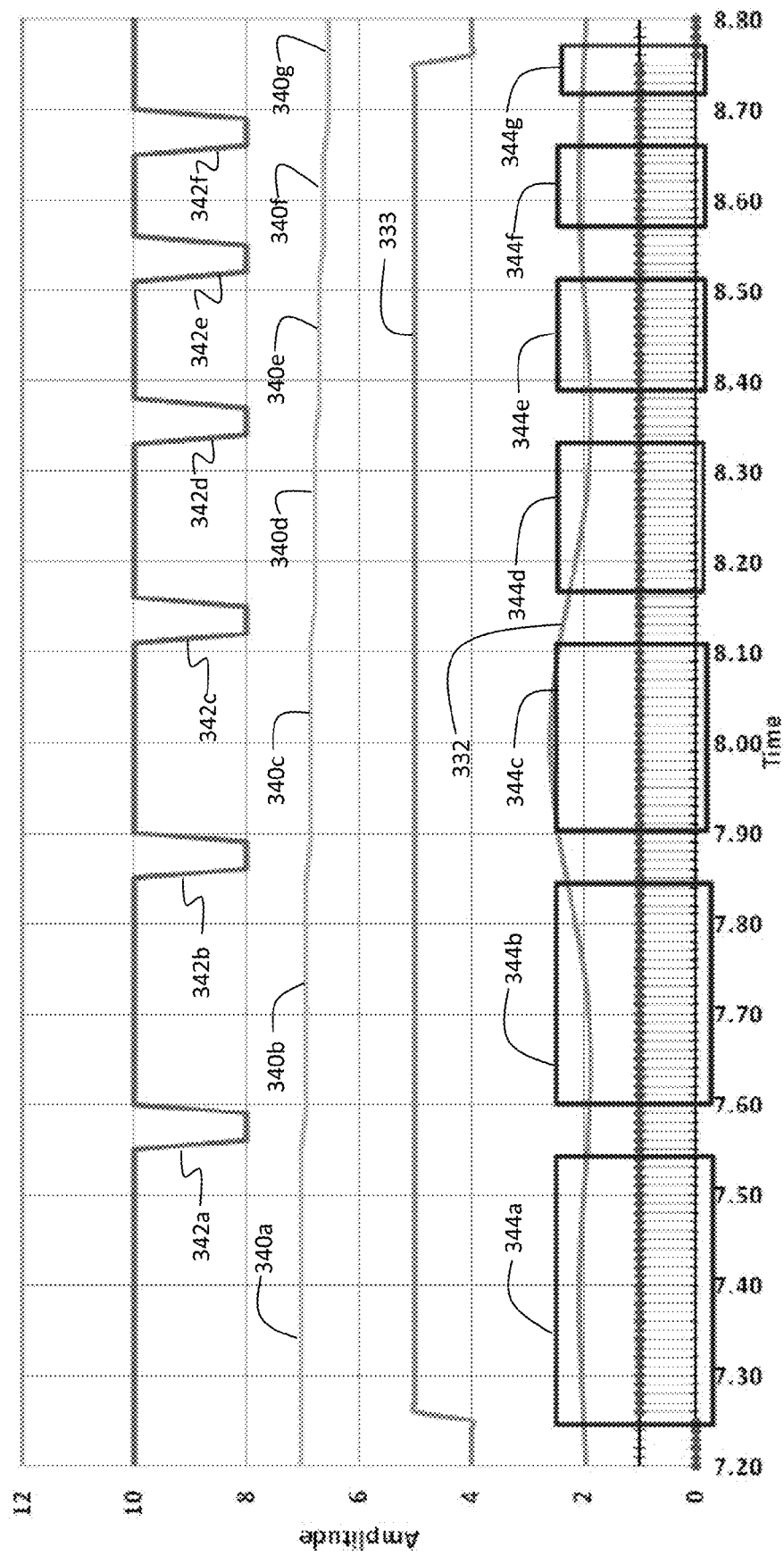
FIG. 5 is an example of a timing diagram for the claimed method, designed to acquire multiple measures of a select set of k-values, with a different number of samples acquired at each k-value to counteract the decrease in energy density at increasing k-value.

A consistent number of samples at each k-value can be acquired, or an alternative sequence may be employed where, as k-values decrease, hence increasing in signal amplitude, fewer samples are acquired. A pulse sequence designed for this type of acquisition is illustrated in FIG. 5. Multiple samples of each k-value targeted in the acquisition are acquired in rapid succession, with all gradients off. These repeats provide the input for signal averaging in low SNR signals. As with the pulse sequence, depicted in FIGS. 3 and 4, the underlying signal is minimally impacted by motion due to the very short time window in which data is acquired for a given k-value.

Samples within the portions of the sample window 344a-344g outlined on FIG. 5 correspond to the number of samples acquired for a given k-value 340a-340g each induced by an unwinding pulse 342a-342f of the k-value selection gradient. $N_k$, the number of samples associated with a given k-value, can be selected based upon expected SNR, tissue contrast, contrast to noise, pathology, texture size, and/or texture bandwidth. For the example in FIG. 5 it can be seen that a decreasing number of samples are taken for progressively smaller k-values (larger textural features). This is because, as previously discussed, to first order signal amplitude increases with decreasing k-value—energy density is generally proportional to $k^{-1}$. For this same reason, larger k-values are acquired first in this scheme, when T2 effects are least, the longer wavelength, higher signal strength, k-values being recorded later in the acquisition.

Refocusing the echo, and/or a new TR can be used to build up a library of k-space samples. Acquisition of multiple k-values within one TR can be facilitated by application of multiple refocusing gradients and/or RF pulses, to increase the time over which the additional k-values can be sampled within a TR. These later echoes would presumably be used to acquire the coefficients of the lower k-values in the selected set, as their energy density in the continuum of values is generally higher so the effect of $T_2$ decay on overall signal magnitude will not affect them as severely as it would the higher k-values. In this way a larger portion of the required k-space filling can be accomplished over fewer TRs, allowing more rapid data acquisition, minimizing the need for repositioning the VOI.

Figure 8:
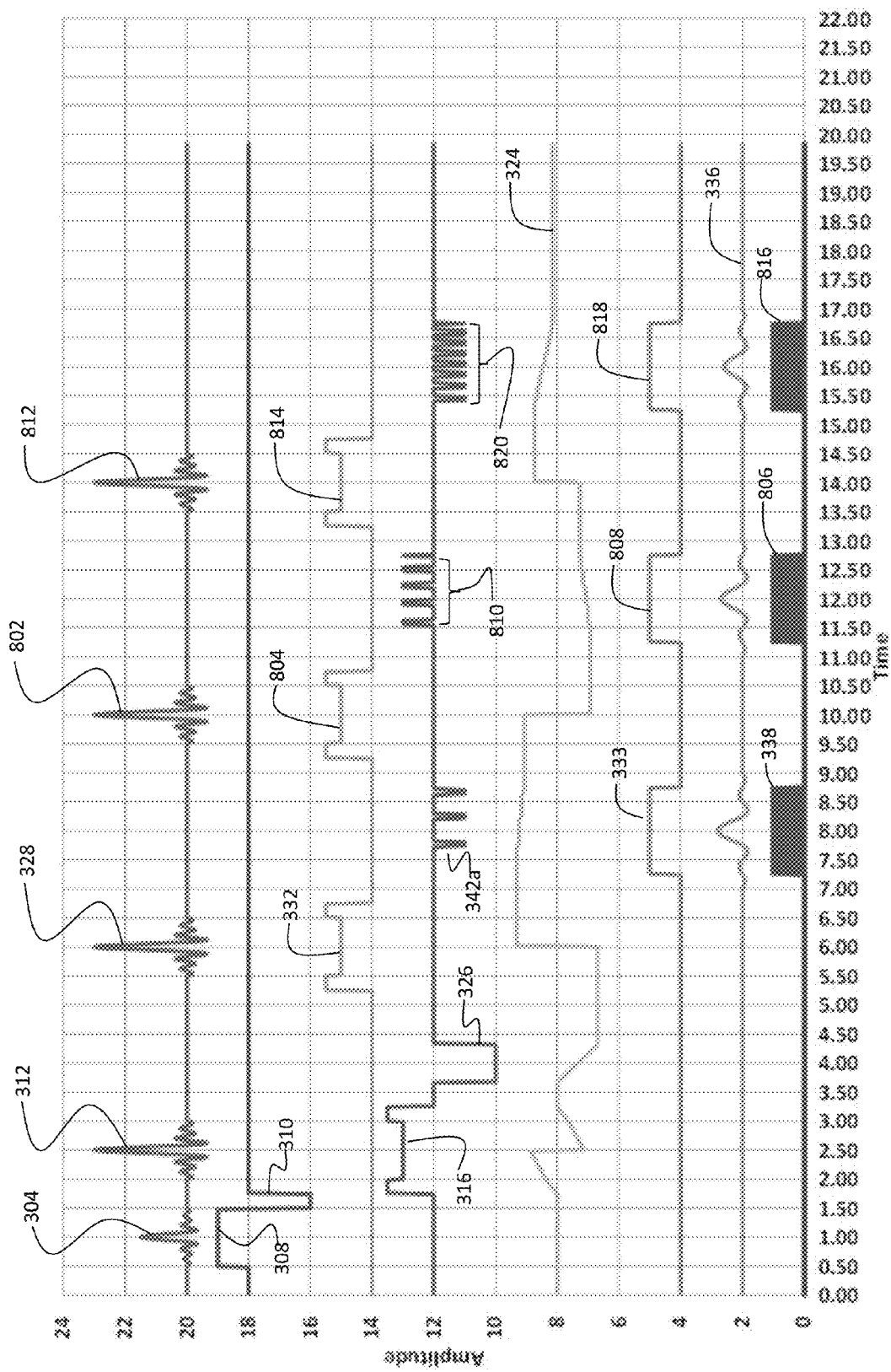
FIG. 8 is an example timing diagram for the claimed method designed to provide data acquisition over multiple refocused echoes within a single TR; and, FIGS. 9A and 9B are a depiction of two possible shapes for the acquisition volume of interest (VOI).

FIG. 8 shows an extension of the basic sequence of the method claimed herein, using spin-echo refocusing to extend the record time for the TR. Application of a refocusing RF pulse 802 with an associated gradient pulse 804 results in slice-selective refocusing. After an appropriate settling time, a second sampling window 806 is opened by the receive gate 808. Multiple k-value selection gradient pulses 810 are applied to increment the selected k-value and, after switching off each successive gradient pulse, multiple samples of the selected k-value are acquired in the sampling window. A second slice-selective refocusing RF pulse 812 with associated gradient pulse 814 again inverts the spins and, after application of each in the multiplicity of k-value selection gradient pulses 820, data is acquired in a third sampling window 816, opened by the receive gate 818. As shown in the drawing, an increasing number of k-values may be sampled with each refocusing. Refocusing can be repeated until the decrease in signal level from T2 and other effects makes further signal acquisition ineffective. Another method to extend the record time by exciting multiple signal echoes, is to use one, or a series of, gradient recalled echoes (GRE). GRE are different from the SE in that they cannot refocus the effects of stationary inhomogeneities, so T2* effects limit the number of repeats.

In addition to the tissue contrast available, the k-values associated with particular pathology will be part of the determination of the number of samples needed for signal averaging, $N_k$. In liver fibrosis, the wavelength of pertinent textures is in the range of 400 microns, i.e. a k-value of 2.5 cycles/mm. This is similar to the textural spacings seen in fibrotic development in many other diseases, such as cardiac fibrosis. The spacing of elements in trabecular bone varies a lot, but the minimum spacing of interest is the width of trabecular elements, which are approximately 80 microns, setting a maximum k-value of 12.5 cycles/mm. In neuropathology, many of the textures of interest are very fine, on the scale of 50 microns, equivalent to a k-value of 20 cycles/mm.

Each pathology will dictate what exactly is needed as quantitative data, i.e. what part of the continuum of k-values needs to be monitored, and with what resolution and sensitivity. In some pathologies, short (long) wavelength features increase at the expense of long (short) wavelength features (e.g. liver fibrosis). In other pathologies, an amplitude decrease and broadening of short wavelength features indicates disease progression—e.g. degradation of the ordered formation of cortical neuronal minicolumns (approximately 80-micron spacing) with advancing dementia. In bone, with increasing age, first the highest k-value features disappear in the structural spectrum. Next the major structural peaks shift slowly towards lower k-values with advancing osteoporosis, the pace of this shift accelerating as an increasing percentage of trabecular elements thin to the point that they break.

The signal level obtainable will depend on anatomy to some extent. For instance, though the resolution needed is highest in brain, the proximity of the cortex to the surface of the head ensures that use of a surface coil will provide significant signal boost for cortical structures. Lower resolution is required in liver, as the structures of interest are on the order of several hundred, rather than tens of microns. But, the organ is deeper (further from the coil) reducing the measured signal. Using the in-table coil for spine data acquisition yields modest signal level and good stabilization. Also, bone is a high contrast target, so the SNR requirement is not as stringent. For all these reasons, the exact number of repeats needed for averaging depends on more than the k-value range targeted.

Figure 6:
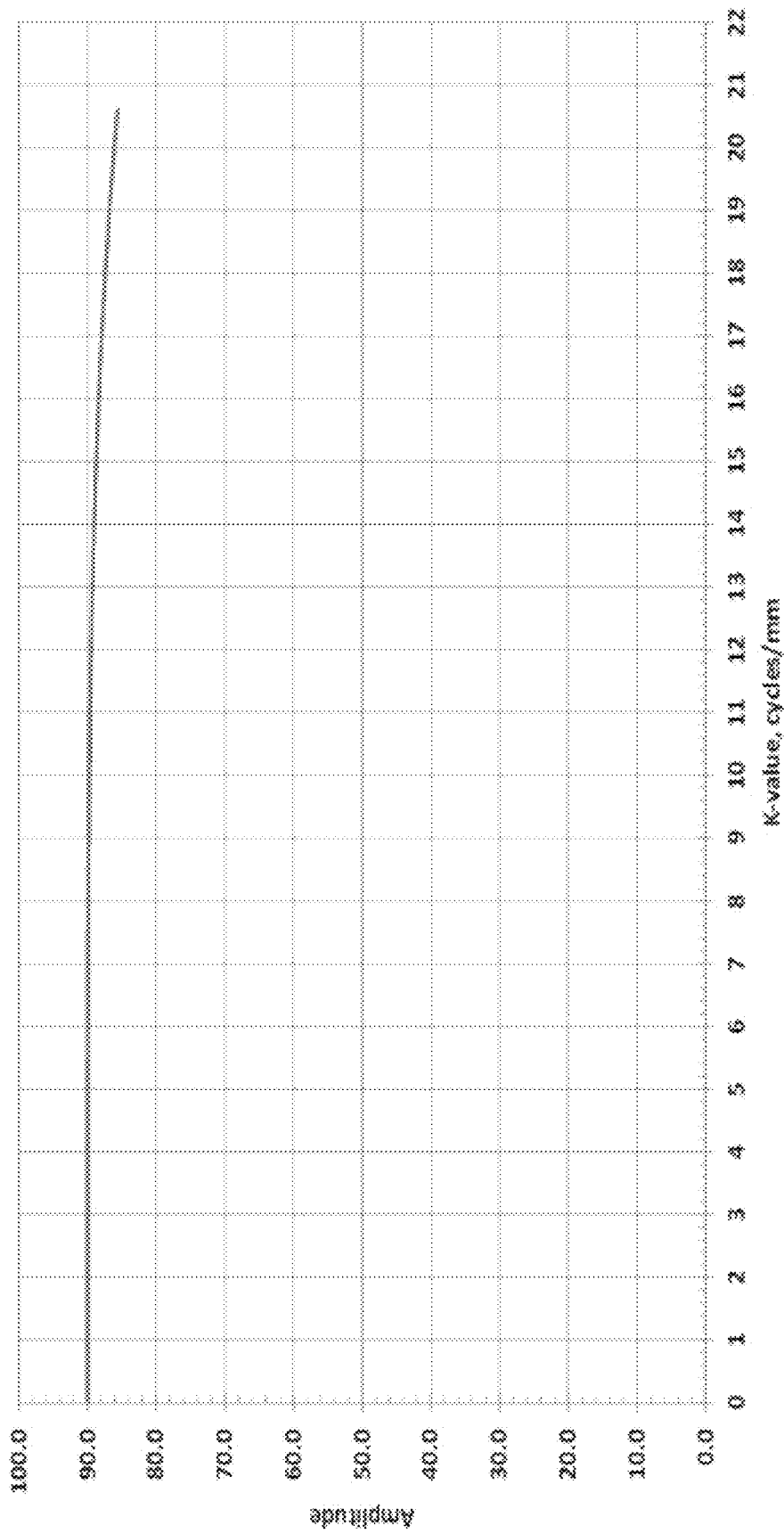
FIG. 6 is a simulation showing that the ability provided by the claimed method to acquire many repeats of a targeted k-value within a single TR enables robust signal averaging to boost SNR.

FIG. 6 shows a simulation demonstrating that the ability provided by the claimed method to acquire many repeats of a targeted k-value within a single TR enables robust signal averaging to boost SNR. Assuming a subject displacement rate (which has in practice been measured clinically over the course of several scans) of 30 μm/sec, and a sampling rate=33.3 kHz (ΔTsample=30 μs), 90 repeat samples for averaging can be taken rapidly enough that, even up to a k-value of 20 cycles/mm (texture wavelength=50 μm), the acquisition remains immune to motion effects.

Figure 7:
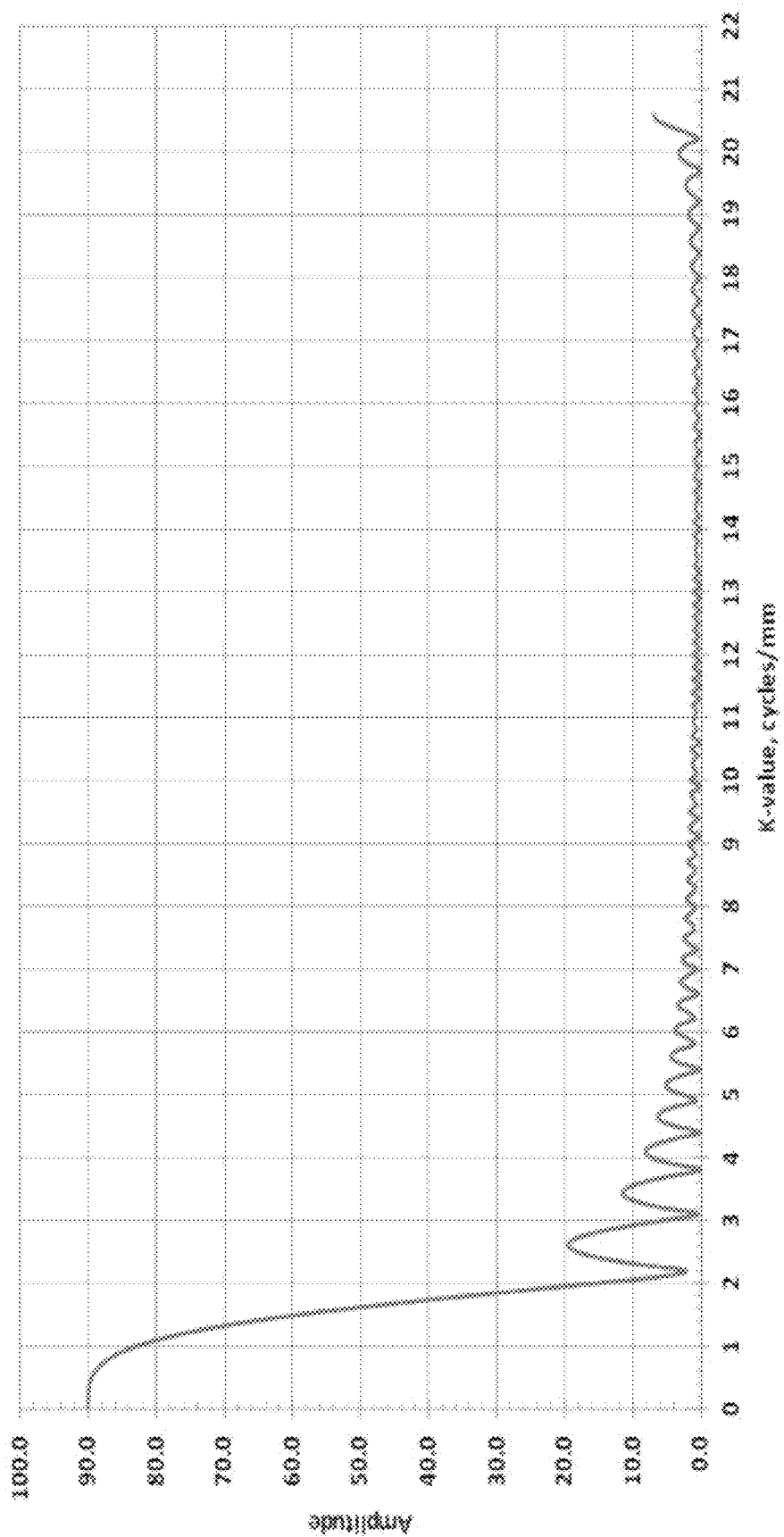
FIG. 7 is a simulation showing the results of attempting to acquire 90 samples for averaging using the conventional frequency-encoded echo approach, wherein acquisition of only a small number of repeats of a particular k-value are possible in each TR due to the long record time for each echo.

FIG. 7 shows that, for comparison, using the conventional approach of acquisition of a spatially encoded echo, even assuming a relatively fast gradient refocus sequence, which would provide a sampling rate of about 67 Hz (ΔTsample=15 msec), subject motion over the time needed for 90 repeats would severely degrade the signal, and any ability to improve SNR by signal averaging. The situation is actually worse due to the fact that to acquire 90 repeats using conventional spatially-encoded echoes would require several TRs, making the acquisition time significantly longer, and the signal degradation due to motion much more severe. With the exception of the very lowest k-values, the potential SNR gain due to multiple sample combination has been nullified by the effects of motion.

By acquisition of a large enough selected range of k-values, construction of a structural profile in one or more dimensions becomes a possibility. As discussed above, refocusing echoes within a single TR, or multiple TRs, can be used to build up a library of k-space samples. Phase coherence might not be maintained between different k-values if they are acquired in TRs separated temporally such that displacement has occurred between them. If our primary interest is in the relative strength of signals at particular k-values, this is not a problem. If creation of a profile or an image from this library of values is desired, the necessary post processing will have as input the high SNR measure obtained within each TR using the method claimed herein. These measures can then provide robust input for any required reregistration between echoes or TRs towards constructing a profile. As an example selection and measurement in a first TR of a set of selected k-values may be accomplished with at least one having a low k-value. In a subsequent TR, selection of the same set of k-values will allow re-registration of the data between the two TRs since even if significant motion has occurred the phase change in the low k-value phase shift will be less than for higher k-value textures and may be correlated between the two TRs. Basically, the higher the k-value, the greater the phase shift due to subject motion. Acquiring signal from successive encodes with a large difference in k-value enables a better estimate of phase shift by careful comparison of the apparent phase shift for each.

This is very similar to x-ray diffraction, wherein the magnitude-only information (no phase) obtained presents the challenge of determining a best estimate of the corresponding structural profile based on this magnitude-only information. Algorithms exist towards solving the problem, the chance of success depending on the range of k-value coefficients obtained, the SNR of each averaged coefficient, and the width of values contained in a nominally single-valued acquisition of k-value. The chance of success in this effort is greatly increased using the claimed method due to its immunity to subject motion.

The ability to reconstruct a profile from k-value data depends somewhat on the spectral broadness of each single-k-value acquisition. While this is influenced by the VOI (Volume of Interest) size and shape, it is also influenced by k-value and pathology, as degradation of tissue often tends to lead to more textural randomness within tissue.

Selection of the VOI—shape, dimensions, orientation, and positioning within an organ/anatomy affects the data measured and its interpretation. The VOI shape can be chosen to maximize usefulness of the acquired data. Data can be acquired in different directions, and at different textural wavelengths (k-values) within a VOI enabling assessment of textural anisotropy. Texture can be sampled in multiple VOIs, either interleaved within a single TR, or in successive TRs, towards assessment of pathology variation across an organ. Standard interleaving processes for the VOI may be used within a TR to provide additional data by applying additional encoding pulses on vector combination gradients and associated k-value selection gradient pulses for k-values in the interleaved VOI. As previously described, additional excitation RF pulses with associated slice selection gradients may be repeated within the same TR by exciting a volume of interest with a gradient set in each repeat having at least a first gradient with an alternative orientation from the first gradient pulse 308 applied initially in the TR, to define an additional VOI for excitation in new tissue, that does not overlap any previous VOI in the TR (fourth, fifth and sixth gradients in a first repeat and succeeding incremental gradients in subsequent repeats). This response can be mapped, or the several measures taken and averaged, whatever is appropriate for the targeted pathology. This is similar to the multi-positioning of tissue biopsy. However, in the case of tissue biopsy, the number of repeats is limited due to the highly invasive nature of the technique. The minimum number of structural oscillations to be sampled at a specific k-value dictates a minimum VOI dimension in the direction of sampling—the length required varying inversely with targeted k-value.

To ensure adequate sampling of structure when targeting a range of k-values, the VOI dimension in the sampled direction can be held constant for all k-values in the targeted range, with the result that the number of structural oscillations sampled will vary with k-value. This is a simple solution, requiring the sampling dimension be set by the lowest k-value (longest wavelength structure). Using this approach, the sampling dimension of the VOI is larger than required for the highest k-value in the range, thus providing less localization within the tissue than would be otherwise possible.

Alternatively, data at widely differing k-values can be acquired in successive TRs, using changing VOIs tailored to the specific k-value targeted. Or, the dimensions of the VOI can be selected such that acquisition in different directions within the VOI will be tailored to sampling in a specific textural frequency (k-value) range.

Similarly, the VOI may be held constant and the vector combination gradient for the encoding and k-selection pulses may be altered from TR to TR for assessing feature size.

Figure 9A:
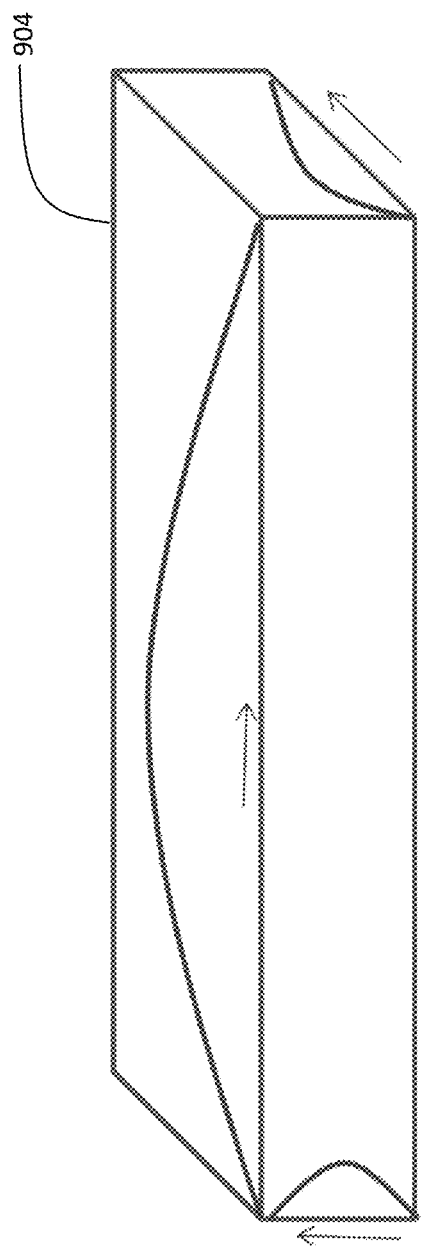
Figure 9B:
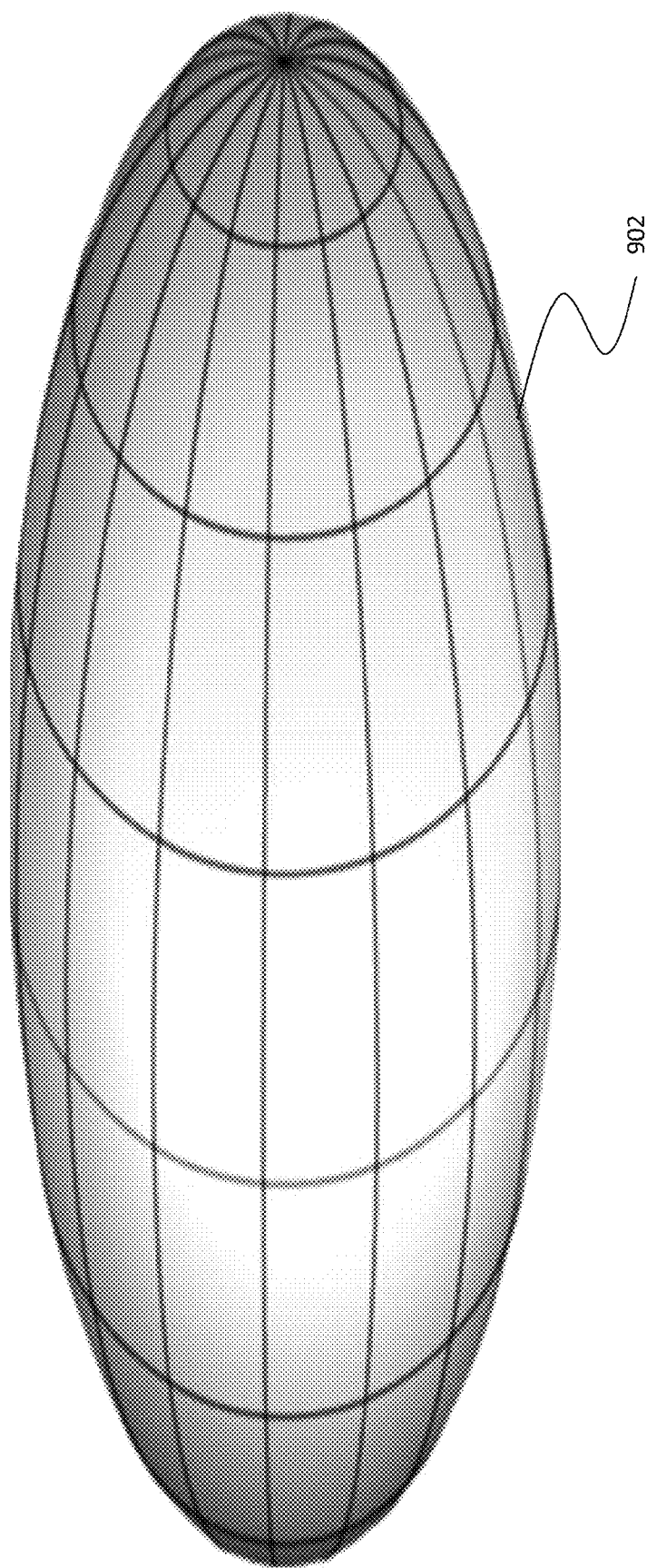

In some instances, it is desired to localize tightly in the spatial domain, to broaden the localization in k-space. By defining a non-cubic acquisition volume, it would be possible to acquire data from differing k-values along the different (orthogonal or other) directions within the VOI, within one TR. The elliptical cross-section VOI 902 in FIG. 9B is one such possibility. Acquisition along any radial direction, as well as along the axis of the shape, would be possible within one TR.

Additionally, one could use the flexibility of the method claimed herein to sample k-space in a linear or in a curved trajectory. For example, texture could be sampled along radial lines, or along an arc or a spiral, to extract information of textural sizes along different spatial directions. These methods can be used to determine the anisotropy of texture, or the sensitivity to alignment in structures that are semi-crystalline, such as cortical neuronal columns, or to more rapidly build up a library of k-values within a targeted extent of tissue in an organ.

During one TR (i.e., one 90 degree excitation) k-value encodes can be applied in multiple directions by changing the applied vector combination gradients for encoding and k-selection pulsing. The exact form of the VOI and sampling direction can be used to yield much textural information. For instance, the organization of cortical neuron fiber bundles is semi-crystalline, as the bundles in healthy tissue form in columns. Because of this, the measure of textural spacing perpendicular to the bundles is very sensitive to orientation. When the orientation is exactly normal to the columns, a very sharp signal maximum is expected, the signal falling off rapidly as the orientation varies on in either rotational direction away from this maximum. One way to measure the spacing and organizational integrity (a marker of pathology) would be to "rock" the acquisition axis around this maximum looking for a resonance in signal intensity. This approach of looking for "textural resonances" by looking for signal maxima can be applied in any tissue region. As pathology degrades the organizational integrity, the sharpness of this peak will degrade and the signal maximum will be reduced.

Similarly, the randomness of the spacing in certain textures can be assessed by varying the length of tissue sampled in a specific, or in multiple directions, with subsequent change in acquisition length. The selected value for that length can be varied over multiple TRs to test the sensitivity of the measured coefficient to this parameter.

The VOI can be selectively excited by a number of methods, for instance intersecting slice-selective refocusing, selective excitation using phased-array transmit in combination with appropriate gradients, adiabatic pulse excitation to scramble signal from the tissue outside the region of interest, as examples. Parameter selection for the various methods can be done with SNR optimization in mind. For instance, the VOI generated by a slice selective excitation and two additional mutually-orthogonal slice selective refocusing pulses, as by VOI 904 in FIG. 9A. Through careful RF pulse design, the shape of the VOI can be designed so that the edges are smooth and more approximate a windowing function, as shown in FIG. 9B. These windowing functions provide the volume selection without adverse impact on the spatial frequencies. Recall, in Fourier theory, each spectral line is smeared by the convolution of a Fourier transform of the window function. We want to minimize this smearing of the underlying spectrum, as it decreases the energy spectral density, and adversely impacts SNR.

Importantly, as has been discussed previously, the VOI can be moved from place to place within an organ or anatomy under study to measure the variation of texture/pathology. This response can be mapped, or the several measures taken and averaged, as appropriate for the targeted pathology. This is similar to the multi-positioning of tissue biopsy. However, in the case of tissue biopsy, the number of repeats is limited due to the highly invasive nature of the technique.

Different diseases and conditions affect tissue in different ways. Generally, pathology advancement entails: 1) a loss of energy density in specific regions of k-space, and/or 2) a shift in textural energy density from one part of k-space to another, both effects being accompanied by 3) changes in the width of existing peaks in the continuum of textural k-values. Using trabecular structure as an example—with decreasing bone health the average separation of trabecular elements widens (texture shifts to lower k-values) and becomes more amorphous (broader peaks in k-space), while in parallel the structural elements thin (a shift to higher k-values in a different part of the spectrum). Other tissues/organs are affected by diseases that have their own individual signatures in tissue texture.

Using the method claimed herein, k-space is probed to reveal texture in such a way as to eliminate the loss of signal resolution that results from subject motion blurring. Instead of measuring the large continuum of k-values needed to create an image, the focus here is on acquisition of a select few k-values per TR, with sufficient repeats of each to yield high SNR. Each of the individual acquisitions is centered on a single k-value. While the spatial encode is, to first order, a single spatial frequency sinusoidal encode, there are a number of factors which have the effect of broadening the spatial frequency selectivity of the k-value measurement. One significant factor affecting the broadness, or bandwidth, of the k-value measurement is the length of the sampled tissue region. A longer sampling length encompasses more textural wavelengths along the sampled direction, which has the effect of narrowing the bandwidth of the k-value measurement. (This is the inverse relationship between extent of a measurement in real and in k-space.) Hence, an aspect of the claimed method is the ability to set the bandwidth of the k-value measurements by appropriate selection of the sampling length within the VOI. Using this method, the bandwidth of the measurement can be set according to the desired k-space resolution appropriate to the tissue being evaluated. (Need both high k-values for good texture resolution, and high resolution in k-space for sensitive monitoring of pathology-induced changes.) For highly ordered structures one could choose a set of narrow bandwidth measurements distributed over the expected range of texture wavelengths, whereas in a more randomly ordered structure, such as the development of fibrotic texture in liver disease, one could choose to use a single, or a few, broadband k-value measurements to monitor development of the fibrotic texture.

A measure of both the relative intensities of the various textural k-values in a tissue and the broadness of the peaks along the continuum of textural k-values present within the texture under study is needed. As such, data acquisition can be designed to probe specific region(s) of k-space, with parameter selection that will enable measurement of the relative width of peaks arising from the underlying tissue, rather than that resulting from experiment parameters. It is necessary to recognize the interaction of the two components, and design experiments to yield the best measure of pathology-induced tissue changes.

Keeping in mind the inverse relationship between localization in real and in k-space, and using the example of bone again: Trabecular elements are on the order of 80 microns in width, hence a large range of finely-sampled k-values is required to monitor their thinning. To achieve fine sampling of each k-value (good localization in k-space) a long sampled region in tissue space would be required.

The ability to tailor the width of the peak in k-space by varying the length of tissue sampled suggests various approaches, all possible while meeting the requirement for rapid acquisition of repeat measures of individual k-values to ensure motion immunity. For instance, the general distribution of textural frequencies present in the tissue can be measured using broad, overlapping peaks in k-space. Then VOI dimensions can be varied to allow greater resolution in k-space to determine, with high sensitivity, the distribution of k-values/textural frequencies present in the tissue.

An additional feature of the method claimed herein is that, while enabling the motion immunity needed for robust assessment of pathology, contrast can also be improved through application of the claimed method in conjunction with appropriately selected and implemented contrast mechanisms. The method is such that combination with many pertinent contrast mechanisms is easily accomplished.

Though a good SNR level is needed, another very important figure in MR imaging is contrast to noise (C/N). A large signal is of little benefit if there is no contrast to highlight the structures of interest against the surrounding tissue, whether it be negative or positive contrast. As discussed above, the magnetic resonance modality allows tuning of contrast to highlight tissue structures/morphology under study. For instance, T1 contrast can be used to highlight fat, T2* provides contrast to the hemoglobin in blood, T2 contrast can be used to highlight water containing tissue/sera. A range of other contrast mechanisms have been developed for this modality, such as Blood Oxygenation Level Dependent (BOLD) contrast, Dynamic Susceptibility Contrast (DSC) imaging, and Arterial Spin Labeling (ASL) to name a few.

In these contrast schemes blood, labeled either magnetically or through use of a contrast agent, flows through the anatomical region under study. Rapid image acquisition is done over the time period during which this bolus of labeled blood courses through the targeted brain area/vasculature or changes with time due to local metabolic or other processes. By incorporating the claimed method into these schemes, changes in texture vs. time can be determined with high spatial and temporal resolution.

Additionally, diagnostic boundaries in many diseases are being extended through combination of multiple imaging methods. Use of both differing techniques within a single modality—structural MR, functional MR, DWI (Diffusion Weighted Imaging), DTI (Diffusion Tensor)-MRI—and differing modalities—MR combined with PET (Positron Emission Tomography), CT (Computed Tomography), etc.—yields more information than any one technique could on its own. In this way, traction is being gained in early diagnosis of a range of diseases/pathologies. Advancement in diagnostic science is often from a new technique that can, along with providing valuable diagnostic information pertinent to a particular pathology in its own right, complement current and emerging practice.

As an example, diagnosis and monitoring of ischemic stroke has been greatly facilitated by combining DWI-MRI with standard structural MR imaging. Current studies link MR functional contrast from Blood Oxygenation Level Dependent (BOLD) imaging with both structural MR images and DWI-MRI images. Structural MR image segmentation techniques are used to assess cortical tissue degradation; this information is then combined with both glucose metabolism and amyloid plaque deposition information derived from PET studies. PET is combined with anatomical MRI and with CT in cancer diagnosis.

The increasing range of techniques/contrast mechanisms available in MRI enables combining different diagnostic measurements/techniques within one exam, facilitating data comparison.

DWI, a measure of the voxel-averaged rate of diffusion of water molecules in the target tissue, has increased in use significantly in recent years, as has the derivative technique DTI which assesses the directional anisotropy in the diffusion process. The main clinical domain of application of diffusion imaging is neurologic disorders, especially for management of patients with acute stroke. Additionally, in conjunction with structural MRI, diffusion imaging is routinely used to diagnose Creutzfeld-Jakob Disease (CJD), diffuse axonal injury, evaluate white matter damage in MS, aid in the diagnosis of tumor metastases (breast, prostate, liver), and evaluate tissue changes associated with dementia onset and as an in vivo measure of brain circuitry.

Diffusion imaging provides quantitative information dependent on the voxel-averaged microscopic properties of tissues, such as cell size and shape, packing, etc. through the observation of the diffusion of water molecules. However, many theoretical and experimental analyses of the effect of microscopic tissue properties on diffusion highlight the difficulty in properly interpreting diffusion data to accurately infer the microstructure and microdynamics of biological systems.

Although DWI/DTI is a quantitative measure, it is not a direct measure of these microscopic properties, but is an average over a voxel of several cubic mm. In order to interpret changes in the Average Diffusion Coefficient (ADC) within the voxel, certain assumptions are made, such as tissue homogeneity and type of structure causing the diffusion variation. The exact mechanisms governing water diffusion processes in tissues, especially in the brain, are not clearly understood. What is inferred from the measurement regarding the underlying barriers and restrictions to free diffusion is based on certain assumptions. (ALEXANDER, A., et al.; "Diffusion Tensor Imaging of the Brian"; Neurotherapeutics 4(3), 2007. LE BIHAN, D., JOHANSEN-BERG, H.; "Diffusion MRI at 25: Exploring Brain Tissue Structure and Function"; Neuroimage, Vol. 61, 2012.) Additional information on these underlying structures could help clarify the proper form of these assumptions, adding to the diagnostic accuracy.

The diffusion signal is low and is extremely sensitive to subject motion. Long and high gradients are required to create the diffusion weighted signal, resulting in a long TE, with significant T2 and T2* decay during signal readout, hence low SNR. The strength and duration of the gradients result in high motion sensitivity, as any motion in the gradient direction during the time of gradient application will look like diffusion. (LE BIHAN, D., JOHANSEN-BERG, H.; "Diffusion MRI at 25: Exploring Brain Tissue Structure and Function"; Neuroimage, Vol. 61, 2012.) The signal is sensitive to diffusion time—a long enough diffusion time that water molecules have time to interact with the tissue structure is required. In most clinical situations, diffusion times range between 30 and 50 ms which translates to about 13-17 µm. Any subject motion over that time appears as diffusion on the signal. Further the fast rise/fall time of the gradients results in eddy currents that lead to image misregistration decreasing the SNR. ("A Hitchhiker's Guide to Diffusion Tensor Imaging"; SOARES, J. M., et al.; Frontiers in Neuroscience, 12 Mar. 2013. ALEXANDER, A., et al.; "Diffusion Tensor Imaging of the Brian"; Neurotherapeutics 4(3), 2007. MASCALCHI, M., et al.; "Diffusion-weighted MR of the brain: methodology and clinical application"; Radiologia Medica, 109(3) 2005.)

In contrast to DWI and DTI, the method claimed herein offers a direct measure of very fine (near cellular) texture. As such, it provides valuable complementary diagnostic information as it measures very fine structure, and DWI/DTI measure the effects of that structure on diffusion. Along with the ability of the method claimed herein to provide intricate textural information towards pathology assessment, when used at the front-end of an MR exam that includes DTI it can provide information on the structural boundaries/hindrances in any direction, clarifying interpretation of the DTI signal. Additionally, the method claimed herein enables robust measure of very small scale displacements—it could provide a measure of motion occurring over the course of the DTI acquisition, towards post processing reregistration. The different sequences could, perhaps, be intermingled in time to optimize the effect. Some possible targets for combining the method claimed herein with DTI would be in assessing vasculature in tumors, measuring changes in gray matter with dementia onset. (WESTON, P., et al.; "Diffusion imaging changes in grey matter in Alzheimer's disease: a potential marker of early neurodegeneration"; Alzheimer's Research and Therapy, 7: 47, 2015.), assessing hyperplasiac development of mammary ducting in breast cancer progression, and diagnosis and monitoring of MS, to name a few. The method claimed herein can be applied in tissue regions showing abnormalities in DWI, to measure textural variations indicative of pathology. Measurement of the variation in texture as a function of direction can be further used as an input to guide application of DTI, for correlation with and verification of the the fractional anisotropy measure of DTI.

Arterial Spin Labeling (ASL) is another MR-based technique, which provides a non-invasive measure of cerebral blood flow (CBF) by magnetically labeling blood prior to its movement into the image plane, and then subtracting a background (unlabeled) image. The correspondence between perfusion and metabolism make the technique similar to functional imaging. Research is ongoing into application of the technique to a range of pathologies, including cerebrovascular disease (CVD), dementia, differentiating tumor recurrence from radiation necrosis, and epilepsy. (DETRE, J., et al.; "Applications of Arterial Spin Labeled MRI in the Brain"; Journal of Magnetic Resonance Imaging, 35(5), 2012. PETCHARUNPAISAN, S., et al.; "Arterial spin labeling in neuroimaging"; World Journal of Radiology, 2(10), 2010.)

SNR is low in ASL because the signal from the magnetically labeled water in blood is only about 0.5% to 1.5% of the full tissue signal. A major source of error in perfusion quantification is the arterial transit time from the tagging region to the imaging slice.8 In healthy subjects this is about 1 sec, while it is longer in patients with occluded vessels. As both a background and labeled image must be acquired, subject motion is a serious issue. Also, the 5-10-miute acquisition time makes ASL a somewhat long add-on to an already scheduled clinical exam. Fast acquisition techniques, such as EPI, help somewhat here, but subject motion and low SNR remain a problem. (DETRE, J., et al.; "Applications of Arterial Spin Labeled MRI in the Brain"; Journal of Magnetic Resonance Imaging, 35(5), 2012.) The method claimed herein could provide information on vasculature pathology when used as a complementary technique to ASL-acquired data or in conjunction with ASL contrast. In the latter embodiment, the method claimed herein would use the magnetically labelled blood to heighten contrast, facilitating measurement of changes in vessel texture (vessel density and spatial randomness) as an indicator of pathology such as CVD, tumor, or the vasculature changes attendant with dementia progression.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for selective sampling to assess texture using magnetic resonance (MR) comprising:
   transmitting a first RF pulse with a first gradient chosen for first slice selection;
   transmitting a second RF pulse with application of a second gradient chosen for slice selective refocusing in a region defined by an intersection of the first slice and a second slice;
   encoding a specific k-value with a selected gradient pulse;
   transmitting a third RF pulse with a third gradient activated, said third gradient adapted for slice selective refocusing, defining a region defined by the intersection of the first and second slices and a third slice selection to define a volume of interest (VOI);
   turning off all gradients; and,
   recording multiple samples of an RF signal encoded with the specific k-value in a single TR.

2. The method as defined in claim 1 wherein the step of encoding comprises:
   applying an encoding gradient pulse to induce phase wrap to create a spatial encode for the specific k-value and orientation.

3. The method as defined in claim 2 further comprising:
   issuing a k-value selection pulse on a selected vector combination gradient to determine a second k-value;
   turning off the vector combination gradient; and,
   recording multiple samples of the RF signal at the second k-value in the TR.

4. The method as defined in claim 2 further comprising:
   applying additional k-value selection pulses for a predetermined plurality of pulses on a selected vector combination gradient, each k value selection pulse determining a next k-value;
   turning off the vector combination gradient after each pulse; and,
   recording multiple samples of the RF signal at the next k-value determined by each k value selection pulse in the TR.

5. The method as defined in claim 4 further comprising:
   transmitting a refocusing RF pulse;
   issuing a plurality of k-value selection pulses on the vector combination gradient, each pulse determining to a new k-value;
   turning off the vector combination gradient after each pulse; and,
   recording multiple samples of the RF signal at the next k-value determined by at each k valued selection pulse in the TR.

6. The method as defined in claim 5 further comprising:
   transmitting a second refocusing RF pulse;
   issuing a plurality of k-value selection pulses on the vector combination gradient, each pulse determining a new k-value;
   turning off the vector combination gradient after each pulse; and,
   receiving multiple samples of the RF signal at the next k-value determined by at each k value selection pulse within the TR.

7. The method as defined in claim 4 further comprising:
   applying a refocusing gradient on one of the first, second or third gradients;
   issuing a plurality of k-value selection pulses on the vector combination gradient, each pulse determining a new k-value;
   turning off the vector combination gradient after each pulse; and,
   receiving multiple samples of the RF signal at the next k-value determined by at each k value selection pulse within the TR.

8. The method as defined in claim 4 wherein the number of samples at each new k-value following each of the plurality of k-value selection pulses on the vector combination gradient is selected based upon expected SNR, pathology, tissue contrast, texture size or texture bandwidth.

9. The method as defined in claim 1 wherein the volume of interest is selected using the set of intersecting slice-selective refocusing, selective excitation using phased-array transmit in combination with appropriate gradients, adiabatic pulse excitation to scramble signal from the tissue outside a region of interest outer volume suppression sequences, and other methods of selectively exciting spins in an internal volume including physically isolating the tissue of interest.

10. The method as defined in claim 1 wherein the steps of transmitting a first RF pulse with a first gradient, transmitting a second RF pulse with a second gradient, encoding a specific k-value, transmitting a third RF pulse with a third gradient activated, turning off all gradients and recording samples of an RF Signal at the specific k-value are repeated multiple times in succeeding TR to build a magnitude power spectrum, the specific k-values in each TR independent of intervening motion if constrained within the volume of interest for each TR.

11. The method as defined in claim 1 wherein the steps of transmitting a first RF pulse with a first gradient, transmitting a second RF pulse with a second gradient, encoding a specific k-value, transmitting a third RF pulse with a third gradient activated, turning off all gradients and recording samples of an RF Signal at the specific k-value are repeated multiple times in succeeding TRs with variation of the volume of interest thereby acquiring textural data to assess a textural variation within or across an organ or anatomy.

12. The method as defined in claim 1 wherein the steps of transmitting a first RF pulse with a first gradient, transmitting a second RF pulse with a second gradient, encoding a specific k-value, transmitting a third RF pulse with a third gradient activated, turning off all gradients and recording samples of an RF Signal at the specific k-value are repeated multiple times in succeeding TRs with alteration of a selected vector combination gradient for the selected gradient pulse to assess feature size.

13. The method as defined in claim 2 wherein the steps of transmitting a first RF pulse with a first gradient, transmitting a second RF pulse with a second gradient, encoding a specific k-value, transmitting a third RF pulse with a third gradient activated, turning off all gradients and recording samples of an RF signal at the specific k-value are repeated multiple times within the TR, wherein the steps of transmitting a first RF pulse with a first gradient, transmitting a second RF pulse with a second gradient, and transmitting a third RF pulse with a third gradient activated, are accomplished with a gradient set in each repeat having at least a first gradient with an alternative value to define an additional VOI for excitation in new tissue, that does not overlap any previous VOI in the TR.

14. The method as defined in claim 2 wherein the encoding gradient pulse is set to zero.

15. The method as defined in claim 4 further comprising:
selecting combinations of the first, second and next k-values obtained in the TR;
reregistering selection of the volume of interest based on the selected combinations for a subsequent TR.

16. The method of claim 3 wherein the specific k-value and the second k-value are chosen with at least one of the specific k-value and second k-value being low and further comprising:
in a second TR
encoding the specific k-value with an encoding gradient pulse;
turning off all gradients;
recording a second set of multiple samples of an RF signal encoded with the specific k-value;
issuing a k-value selection pulse on the selected vector combination gradient for the second k-value;
turning off the vector combination gradient; and,
recording a second set of multiple samples of the RF signal at the second k-value; and,
re-registering the recorded multiple samples of the RF signal at the specific k-value and the second set of recorded multiple samples of the RF signal at the specific k-value and the recorded multiple samples of the RF signal at the second k-value and the second set of recorded multiple samples of the RF signal at the second k-value based on correlation of data for the low k-value.

17. The method as defined in claim 1 further comprising selecting a narrow bandwidth to allow single species signal acquisition for enhanced k-value.

18. A method for selective sampling to assess texture using magnetic resonance (MR) comprising:
transmitting a first RF pulse with a first gradient chosen for first slice selection;
transmitting a second RF pulse with application of a second gradient chosen for slice selective refocusing in a region defined by an intersection of the first slice and a second slice;
applying an encoding gradient pulse to induce phase wrap to create a spatial encode for a specific k-value and orientation;
transmitting a third RF pulse with a third gradient activated, said third gradient adapted for slice selective refocusing, defining a region defined by the intersection of the first and second slices and a third slice selection to define a volume of interest (VOI);
turning off all gradients; and,
recording multiple samples of an RF signal encoded with the specific k-value;
issuing a k-value selection pulse on a selected vector combination gradient to determine a second k-value;
turning off the vector combination gradient; and,
recording multiple samples of the RF signal at the second k-value in a single TR.

19. The method as defined in claim 18 further comprising:
transmitting a fourth RF pulse with a fourth gradient chosen for fourth slice selection;
transmitting a fifth RF pulse with application of a fifth gradient chosen for slice selective refocusing in a region defined by an intersection of the first slice and a second slice;
applying a second encoding gradient pulse to induce phase wrap to create a spatial encode for an additional specific k-value and orientation;
transmitting a sixth RF pulse with a sixth gradient activated, said sixth gradient adapted for slice selective refocusing, defining a region defined by the intersection of the the fourth and fifth slices and a sixth slice selection to define a second separate VOI within the single TR;
turning off all gradients; and,
recording multiple samples of an RF signal encoded with the additional specific k-value;
issuing a k-value selection pulse on a selected vector combination gradient to determine a second additional k-value;
turning off the vector combination gradient; and,
recording multiple samples of the RF signal at the second additional k-value in the single TR.

20. The method as defined in claim 18 wherein the encoding gradient pulse is set to zero.

* * * * *